US012773542B2

(12) United States Patent
Chu et al.

(10) Patent No.: US 12,773,542 B2
(45) Date of Patent: Oct. 27, 2026

(54) BALLOON DILATION INSTRUMENT WITH TRANSLATING GUIDE TIP ELEMENT

(71) Applicant: Acclarent, Inc., Irvine, CA (US)

(72) Inventors: Brittanie Chu, Chino Hills, CA (US); Henry F. Salazar, Pico Rivera, CA (US); Alex Gonzalez, Lake Forest, CA (US); Cesar Fuentes-Ortega, Pasadena, CA (US); Sheila Ruiz, Mission Viejo, CA (US); George Gusein, Acre (IL); Hao H. Tran, Santa Ana, CA (US); Zachary Radner, Anaheim, CA (US)

(73) Assignee: Acclarent, Inc., Irvine, CA (US)

( * ) Notice: Subject to any disclaimer, the term of this patent is extended or adjusted under 35 U.S.C. 154(b) by 89 days.

(21) Appl. No.: 18/594,208

(22) Filed: Mar. 4, 2024

(65) Prior Publication Data

US 2024/0382725 A1 Nov. 21, 2024

Related U.S. Application Data

(60) Provisional application No. 63/467,683, filed on May 19, 2023.

(51) Int. Cl.
*A61M 29/02* (2006.01)

(52) U.S. Cl.
CPC ....... *A61M 29/02* (2013.01); *A61M 2029/025* (2013.01); *A61M 2205/0216* (2013.01); (Continued)

(58) Field of Classification Search
CPC ..... A61B 34/20; A61B 1/233; A61B 17/1688; A61B 2018/00327; A61B 17/12136; (Continued)

(56) References Cited

U.S. PATENT DOCUMENTS 7,720,521 B2 5/2010 Chang et al.
8,282,667 B2 10/2012 Drontle et al.
(Continued)

FOREIGN PATENT DOCUMENTS

EP 3860454 B1 2/2024

OTHER PUBLICATIONS

International Search Report and Written Opinion in Application No. PCT/IB2024/052466, dated Jun. 24, 2024, 17 pages.

*Primary Examiner* — Tan-Uyen T Ho
*Assistant Examiner* — Bridget E. Rabaglia
(74) *Attorney, Agent, or Firm* — Morgan, Lewis & Bockius LLP

(57) ABSTRACT

A dilation catheter is slidably disposed relative to a first guide. A second guide is slidably disposed relative to the first guide and relative to the dilation catheter. The second guide includes an indicator element indicating a position of the distal end of the second guide in three-dimensional space. The second guide positions the indicator element at the distal end of the first guide and remains longitudinally stationary as the dilation catheter translates distally from a proximal position to an intermediate longitudinal position. The second guide translates concomitantly with the dilation catheter as the dilation catheter translates distally from the intermediate longitudinal position to a distal position. The indicator element is positioned with the distal end of the dilation catheter as the dilation catheter translates distally from the intermediate longitudinal position to a distal position.

15 Claims, 21 Drawing Sheets

(52) U.S. Cl.
CPC ..... *A61M 2205/33* (2013.01); *A61M 2209/00* (2013.01); *A61M 2210/0618* (2013.01); *A61M 2210/065* (2013.01); *A61M 2210/0675* (2013.01); *A61M 2210/0681* (2013.01)

(58) Field of Classification Search
CPC ........ A61B 1/00082; A61B 2017/3486; A61B 5/6852; A61B 1/267; A61B 17/24; A61M 29/02; A61M 2210/0681; A61M 25/10; A61M 2029/025; A61M 25/09; A61M 2210/0618; A61M 25/0041; A61M 25/1002; A61M 2210/0675; A61M 25/0662; A61M 2025/0681; A61M 29/00; A61M 31/00; A61M 2025/105; A61M 25/01; A61M 25/1018; A61M 2025/1086; A61M 25/1011; A61M 2025/1072; A61M 2025/1075; A61M 2210/065; A61M 25/104; A61M 25/0136; A61M 25/0113
USPC ......... 606/196, 199, 192, 108, 191, 198, 14, 606/195; 604/96.01, 509, 510
See application file for complete search history.

(56) References Cited

U.S. PATENT DOCUMENTS

| | | | | |
|---|---|---|---|---|
| 8,834,513 | B2 | 9/2014 | Hanson et al. | |
| 9,155,492 | B2 | 10/2015 | Jenkins et al. | |
| 9,192,748 | B2 | 11/2015 | Ressemann et al. | |
| 9,241,834 | B2 | 1/2016 | Chang et al. | |
| 9,579,448 | B2 | 2/2017 | Chow et al. | |
| 9,700,326 | B2 | 7/2017 | Morriss et al. | |
| 9,750,401 | B2 | 9/2017 | Morriss et al. | |
| 9,999,752 | B2 | 6/2018 | Becker | |
| 10,137,286 | B2 | 11/2018 | Lin et al. | |
| 10,206,821 | B2 | 2/2019 | Campbell et al. | |
| 10,463,242 | B2 | 11/2019 | Kesten et al. | |
| 10,561,370 | B2 | 2/2020 | Salazar et al. | |
| 11,013,896 | B2 | 5/2021 | Chan et al. | |
| 11,013,897 | B2 | 5/2021 | Lin et al. | |
| 11,065,061 | B2 | 7/2021 | Makower | |
| 11,103,249 | B2 | 8/2021 | Zoabi et al. | |
| 11,147,908 | B2 | 10/2021 | Drontle et al. | |
| 11,395,906 | B2 | 7/2022 | Palushi et al. | |
| 11,419,623 | B2 | 8/2022 | Palushi et al. | |
| 11,534,192 | B2 | 12/2022 | Goldfarb et al. | |
| 2011/0245886 | A1* | 10/2011 | Stetson .................. | H01R 24/38<br>29/857 |
| 2012/0071857 | A1 | 3/2012 | Goldfarb et al. | |
| 2013/0123833 | A1* | 5/2013 | Lesch ................... | A61M 29/02<br>606/196 |
| 2016/0310714 | A1 | 10/2016 | Jenkins et al. | |
| 2018/0110968 | A1 | 4/2018 | Ngo-Chu et al. | |
| 2018/0264237 | A1* | 9/2018 | Palushi ................ | A61B 5/6851 |
| 2020/0187967 | A1* | 6/2020 | Palushi ............. | A61M 25/1018 |
| 2021/0085402 | A1 | 3/2021 | Salazar et al. | |
| 2021/0361912 | A1 | 11/2021 | Matlock et al. | |

* cited by examiner

BALLOON DILATION INSTRUMENT WITH TRANSLATING GUIDE TIP ELEMENT

PRIORITY

This application claims priority to U.S. Provisional Pat. App. No. 63/467,683, entitled "Balloon Dilation Instrument with Translating Guide Tip Element," filed May 19, 2023, the disclosure of which is incorporated by reference herein, in its entirety.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pat. No. 11,534,192, entitled "Methods and Apparatus for Treating Disorders of the Sinuses," issued Dec. 27, 2022, the disclosure of which is incorporated by reference herein, in its entirety; U.S. Pat. No. 9,579,448, entitled "Balloon Dilation Catheter System for Treatment and Irrigation of the Sinuses," issued Feb. 28, 2017, the disclosure of which is incorporated by reference herein, in its entirety; U.S. Pat. No. 9,155,492, entitled "Sinus Illumination Lightwire Device," issued Oct. 13, 2015, the disclosure of which is incorporated by reference herein, in its entirety; and U.S. Pub. No. 2021/0361912, entitled "Shaft Deflection Control Assembly for ENT Guide Instrument," published Nov. 25, 2021, the disclosure of which is incorporated by reference herein, in its entirety.

In the context of Eustachian tube dilation, a dilation catheter or other dilation instrument may be inserted into the Eustachian tube and then be inflated or otherwise expanded to thereby dilate the Eustachian tube. The dilated Eustachian tube may provide improved ventilation from the nasopharynx to the middle car and further provide improved drainage from the middle car to the nasopharynx. Methods and devices for dilating the Eustachian tube are disclosed in U.S. Pat. No. 10,206,821, entitled "Eustachian Tube Dilation Balloon with Ventilation Path," issued Feb. 19, 2019, the disclosure of which is incorporated by reference herein, in its entirety; and U.S. Pat. No. 11,013,896, entitled "Method and System for Eustachian Tube Dilation," issued May 25, 2021, the disclosure of which is incorporated by reference herein, in its entirety.

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) are used to perform the procedure while the sensors send data to the computer indicating the current position of each surgical instrument. The computer correlates the data it receives from the sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. The surgeon is thus able to know the precise position of each sensor-equipped instrument by viewing the video monitor even if the surgeon is unable to directly visualize the instrument itself at its current location within the body.

In some scenarios, different parts of a medical instrument may be advanced distally and retracted proximally at different stages of operation. It may be desirable to provide position-sensing for the distal-most part of the instrument at the various stages of operation. An example of an arrangement providing such capability is described in U.S. Pat. No. 11,419,623, entitled "Sinuplasty Instrument with Moveable Navigation Sensor," issued Aug. 23, 2022, the disclosure of which is incorporated by reference herein, in its entirety. While several systems and methods have been made and used in connection with IGS navigation systems, it is believed that no one prior to the inventors has made or used the invention described in the appended claims.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Example of an Image Guided Surgery Navigation System

Figure 1:
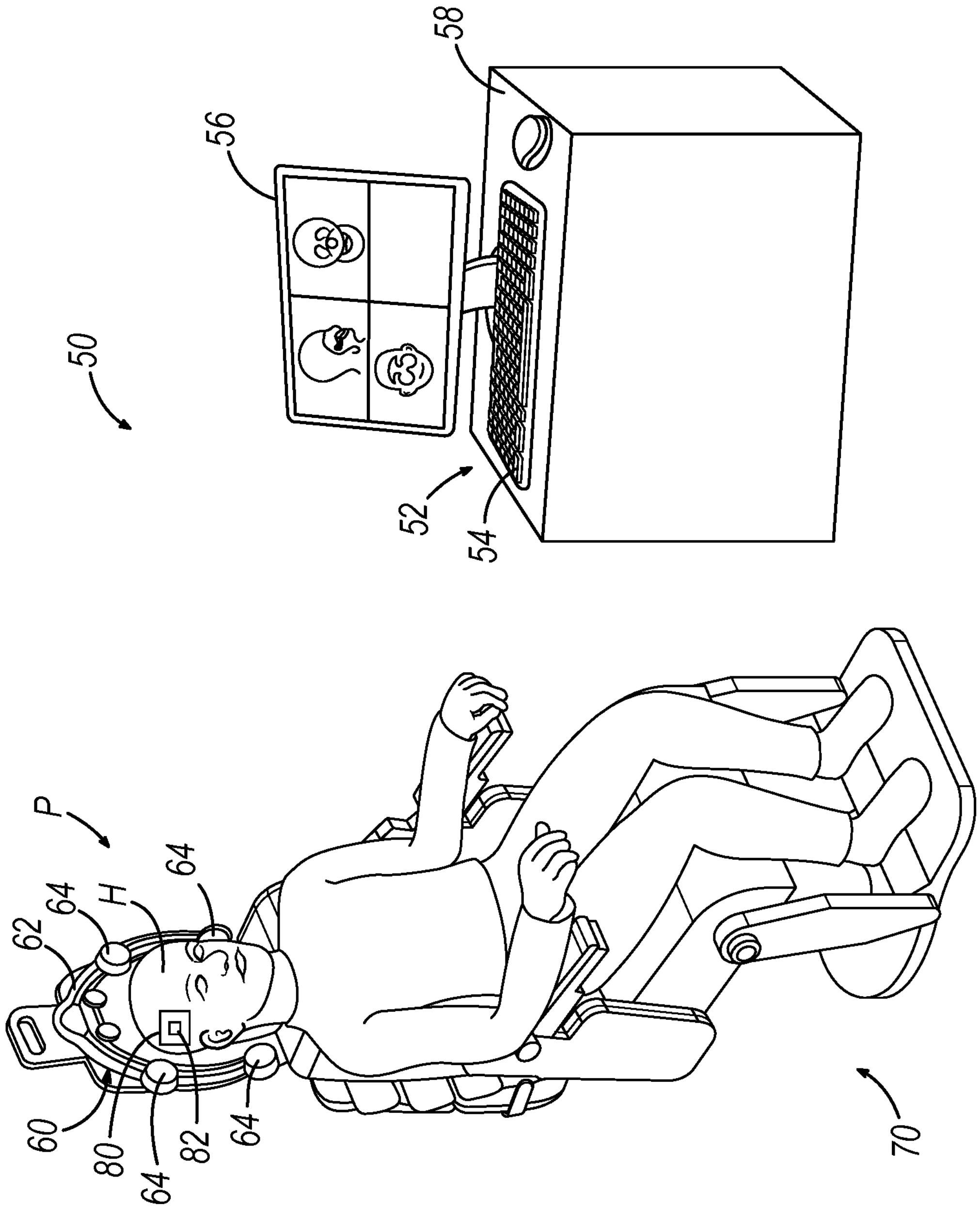
FIG. 1 depicts a schematic view of an example of a surgery navigation system being used on a patient seated in an example of a medical procedure chair.

When performing a medical procedure within a head of a patient (P), it may be desirable to have information regarding the position of an instrument within the head (H) of the patient (P), particularly when the instrument is in a location where it is difficult or impossible to obtain an endoscopic view of a working element of the instrument within the head of the patient (P). FIG. 1 shows an example of an IGS navigation system (50) enabling a medical procedure to be performed within a head (H) of a patient (P) using image guidance. In addition to or in lieu of having the components and operability described herein IGS navigation system (50) may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein, in its entirety; and/or U.S. Pat. No. 11,065,061, entitled "Systems and Methods for Performing Image Guided Procedures within the Ear, Nose, Throat and Paranasal Sinuses," issued Jul. 20, 2021, the disclosure of which is incorporated by reference herein, in its entirety.

IGS navigation system (50) of the present example comprises a field generator assembly (60), which comprises a set of magnetic field generators (64) that are integrated into a horseshoe-shaped frame (62). Field generators (64) are operable to generate alternating magnetic fields of different frequencies around the head (H) of the patient (P). An instrument may be inserted into the head (H) of the patient (P). Such an instrument may include one or more position sensors as described in greater detail below. In the present example, frame (62) is mounted to a chair (70), with the patient (P) being seated in the chair (70) such that frame (62) is located adjacent to the head (H) of the patient (P). By way of example only, chair (70) and/or field generator assembly (60) may be configured and operable in accordance with at least some of the teachings of U.S. Pat. No. 10,561,370, entitled "Apparatus to Secure Field Generating Device to Chair," Issued Feb. 18, 2020, the disclosure of which is incorporated by reference herein, in its entirety. In some other variations, the patient (P) lies on a table; and field generator assembly (60) is positioned on or near the table.

IGS navigation system (50) of the present example further comprises a processor (52), which controls field generators (64) and other elements of IGS navigation system (50). For instance, processor (52) is operable to drive field generators (64) to generate alternating electromagnetic fields; and process signals from the instrument to determine the location of a navigation sensor or position sensor in the instrument within the head (H) of the patient (P). Processor (52) comprises a processing unit (e.g., a set of electronic circuits arranged to evaluate and execute software instructions using combinational logic circuitry or other similar circuitry) communicating with one or more memories. Processor (52) of the present example is mounted in a console (58), which comprises operating controls (54) that include a keypad and/or a pointing device such as a mouse or trackball. A physician uses operating controls (54) to interact with processor (52) while performing the surgical procedure.

While not shown, the instrument that is used with IGS navigation system (50) may include a navigation sensor or position sensor that is responsive to positioning within the alternating magnetic fields generated by field generators (64). A coupling unit (not shown) may be secured to the proximal end of the instrument and may be configured to provide communication of data and other signals between console (58) and the instrument. The coupling unit may provide wired or wireless communication of data and other signals.

In some versions, the navigation sensor or position sensor of the instrument may comprise at least one coil at or near the distal end of the instrument. When such a coil is positioned within an alternating electromagnetic field generated by field generators (64), the alternating magnetic field may generate electrical current in the coil, and this electrical current may be communicated along the electrical conduit(s) in the instrument and further to processor (52) via the coupling unit. This phenomenon may enable IGS navigation system (50) to determine the location of the distal end of the instrument within a three-dimensional space (i.e., within the head (H) of the patient (P), etc.). To accomplish this, processor (52) executes an algorithm to calculate location coordinates of the distal end of the instrument from the position related signals of the coil(s) in the instrument. Thus, a navigation sensor may serve as a position sensor by generating signals indicating the real-time position of the sensor within three-dimensional space.

Processor (52) uses software stored in a memory of processor (52) to calibrate and operate IGS navigation system (50). Such operation includes driving field generators (64), processing data from the instrument, processing data from operating controls (54), and driving display screen (56). In some implementations, operation may also include monitoring and enforcement of one or more safety features or functions of IGS navigation system (50). Processor (52) is further operable to provide video in real time via display screen (56), showing the position of the distal end of the instrument in relation to a video camera image of the patient's head (H), a CT scan image of the patient's head (H), and/or a computer-generated three-dimensional model of the anatomy within and adjacent to the patient's nasal cavity. Display screen (56) may display such images simultaneously and/or superimposed on each other during the surgical procedure. Such displayed images may also include graphical representations of instruments that are inserted in the patient's head (H), such that the operator may view the virtual rendering of the instrument at its actual location in real time. By way of example only, display screen (56) may provide images in accordance with at least some of the teachings of U.S. Pat. No. 10,463,242, entitled "Guidewire Navigation for Sinuplasty," issued Nov. 5, 2019, the disclosure of which is incorporated by reference herein, in its entirety. In the event that the operator is also using an endoscope, the endoscopic image may also be provided on display screen (56). The images provided through display screen (56) may help guide the operator in maneuvering and otherwise manipulating instruments within the patient's head (H).

In the present example, field generators (64) are in fixed positions relative to the head (H) of the patient (P), such that the frame of reference for IGS navigation system (50) (i.e., the electromagnetic field generated by field generators (64))

does not move with the head (H) of the patient (P). In some instances, the head (H) of the patient (P) may not remain completely stationary relative to field generators (64) throughout the duration of a medical procedure, such that it may be desirable to track movement of the head (H) of the patient (P) during a medical procedure. To that end, a patient tracking assembly (80) is secured to the head (H) of the patient (P) in this example. Patient tracking assembly (80) may be secured to the head (H) via an adhesive, via one or more screws, or in any other suitable fashion. Patient tracking assembly (80) includes a position sensor (82), which is in communication with processor (52), such as via a cable (84) (see FIGS. 4-7). In some versions, position sensor (82) is wirelessly coupled with processor (52), such that cable (84) is omitted.

Position sensor (82) is configured to generate signals indicating the real-time position of position sensor (82) in response to an alternating electromagnetic field generated by field generators (64). By way of example only, position sensor (82) may comprise one or more coils. The signals generated by position sensor (82) are communicated to processor (52), such that processor (52) may process signals from position sensor (82) to determine the real-time position of position sensor (82) in three-dimensional space. With patient tracking assembly (80) being firmly secured to the head (H) of the patient (P), patient tracking assembly (80) may move unitarily with the head (H) of the patient (P). Accordingly, signals from position sensor (82) may effectively indicate the real-time position of the head (H) of the patient in three-dimensional space.

After patient tracking assembly (80) is secured to the head (H) of the patient (P), an operator may insert one or more position sensor equipped medical instruments (e.g., ENT shaver, suction cannula, balloon dilation catheter, electrosurgical instrument, etc.) into the head (H) of the patient (P). Signals from position sensors of such instruments may be communicated to processor (52), thereby enabling processor (52) to determine the real-time positions of such instruments in three-dimensional space. With processor (52) knowing the real-time position of the head (H) of the patient (P) in three-dimensional space based on signals from position sensor (82), and with processor (52) knowing the real-time position of a medical instrument in three-dimensional space based on signals from one or more position sensors in the medical instrument, processor (52) may accurately determine the real-time position of the medical instrument in the head (H) of the patient (P). Processor (52) may thereby drive display screen (56) to display an indicator (e.g., crosshairs, etc.) showing the real-time position of the medical instrument in the head (H) of the patient (P) as described above. By way of example only, processor (52) may drive display screen (56) to display an indicator (e.g., crosshairs, etc.) to show the real-time position of the medical instrument in the head (H) of the patient (P) as an overlay on one or more images of at least a portion of the head (H) of the patient (P).

II. Example of Dilation Instrument with Translating Guide Tip Element

In some scenarios, it may be desirable to advance a dilation catheter into an anatomical passageway in or near the car, nose, or throat of a patient; and expand the dilator to thereby dilate the passageway. For instance, it may be desirable to dilate a paranasal sinus ostium or other passageway associated with drainage of a paranasal sinus cavity, a Eustachian tube, a stenotic region in an airway of a patient, etc.

To the extent that an endoscope may be used to provide some degree of visualization within the car, nose or throat of the patient, the nature of the anatomy may substantially restrict the field that is viewable by the endoscope. It may therefore be desirable to provide some other features to promote proper positioning of the dilator within the targeted anatomical passageway. For instance, the instrument may include a position sensor that generates signals indicating the location of the position sensor in three-dimensional space, such that IGS navigation system (50) may be utilized to provide the operator with feedback indicating the real-time position of one or more features of the instrument in three-dimensional space. In addition, or in the alternative, the instrument may include an illuminating feature that is operable to transmit light through the skin of the patient (e.g., from within a frontal sinus cavity or maxillary sinus cavity, etc.); such that the transillumination may also provide feedback to the operator indicating where part of the medical instrument is positioned in real time.

Some dilation instruments may include a dilation catheter that is operable to be advanced distally relative to a guide feature (e.g., a guide rail or guide catheter, etc.). In some scenarios, the distal end of the dilation catheter is positioned proximally relative to the distal end of the guide feature as the guide feature is initially advanced to a point near the anatomical passageway targeted for dilation. After the distal end of the guide feature reaches a desired position, the dilation catheter may be advanced distally relative to the guide feature, such that the distal end of the dilation catheter enters the targeted anatomical passageway and is positioned distally relative to the distal end of the guide feature. In such scenarios, it may be desirable to first obtain feedback indicating the real time position of the distal end of the guide feature in three-dimensional space while the dilation catheter is in the proximal position; then obtain feedback indicating the real time position of the distal end of the dilation catheter in three-dimensional space while the dilation catheter is in the distal position.

To the extent that it may be possible to include a first navigation element (e.g., first position sensor or first illumination source, etc.) at the distal tip of the guide element and a second navigation element (e.g., second position sensor or first illumination source, etc.) at the distal tip of the dilation catheter, it may be desirable to avoid including two navigation elements to thereby reduce cost and complexity of the instrument. The following provides examples of various arrangements where a single navigation element may be used to provide feedback indicating the real time position of the distal end of a guide feature in three-dimensional space while a dilation catheter is in the proximal position; then obtain feedback indicating the real time position of the distal end of the dilation catheter in three-dimensional space while the dilation catheter is in the distal position.

A. Example of Dilation Instrument with Frictionally Interlocking Dilation Catheter Actuator and Guide Element Actuator FIGS. 2A-2E show an example of a dilation instrument (100) that may be used to dilate an anatomical passageway in or near an ear, nose, or throat of a patient. Instrument (100) of this example includes a body assembly (110) and a shaft assembly (150). Body assembly (110) includes a first housing (112), a second housing (114), and a dilation catheter actuator (120). Dilation catheter actuator (120) is slidably disposed in a slot (116) formed in second housing (114). Dilation catheter actuator (120) is operable to drive longitudinal movement of a dilation catheter (160) and a guide element (180) as described in greater detail below.

Figure 4:
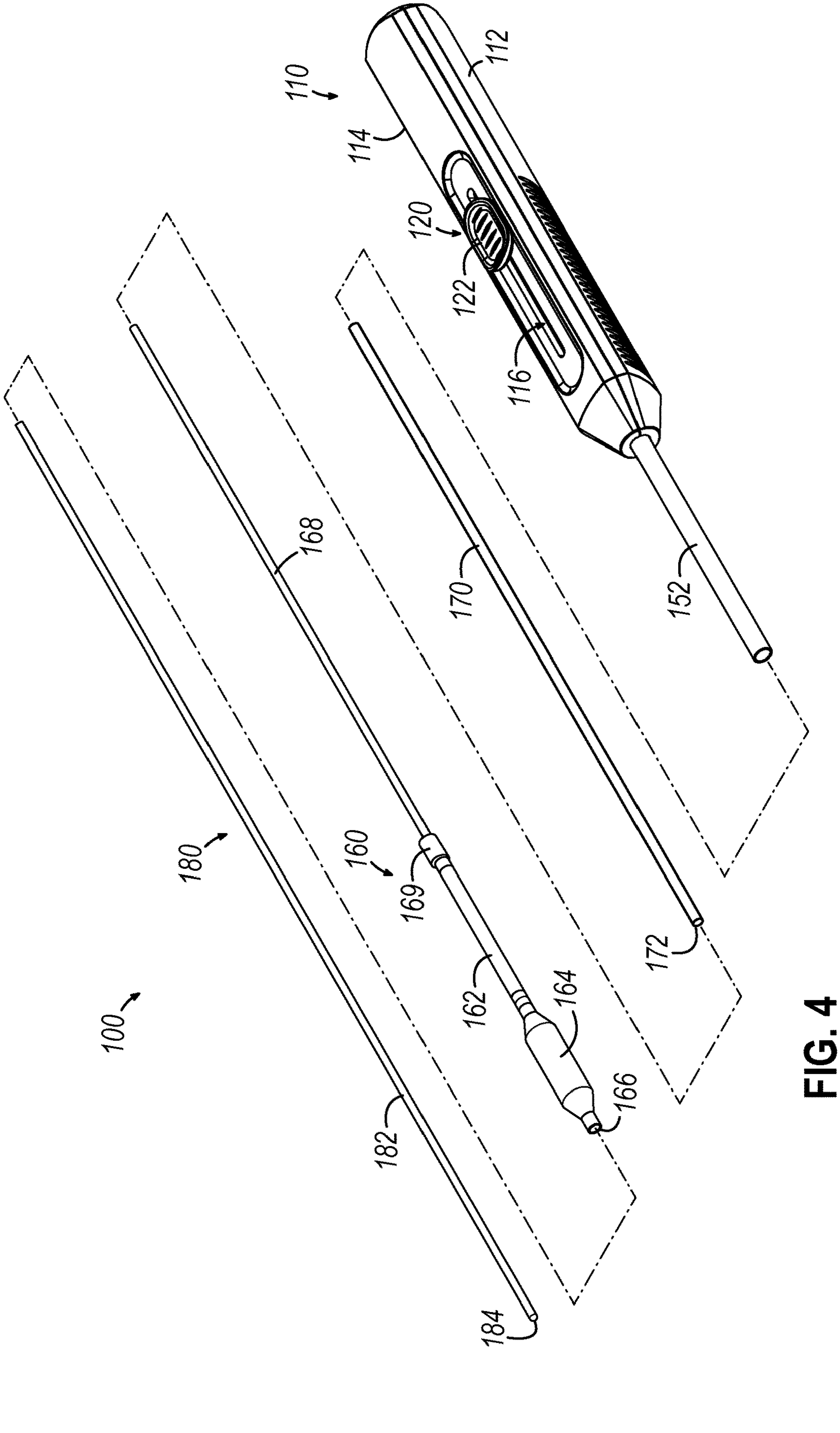
FIG. 4 depicts a perspective view of the dilation instrument of FIG. 2A, with the shaft assembly exploded.

Shaft assembly (150) includes an outer sheath (152), a guide rail (170), dilation catheter (160), and guide element (180). As best seen in FIG. 4, these components are configured to be positioned coaxially with each other, such that outer sheath (152) is positioned externally, dilation catheter (160) is positioned internal to outer sheath (152), guide rail (170) is positioned internal to dilation catheter (160), and guide element (180) is positioned internal to guide rail (170). Outer sheath (152) of the present example is rigid, though other versions may be malleable or otherwise flexible. In the present example, outer sheath (152) does not enter the head (H) of the patient (P) during operation of instrument (100), though some scenarios may exist where outer sheath (152) enters the patient (P) during operation of instrument (100).

Guide rail (170) of the present example is malleable and has an atraumatic distal tip (172). In some versions, distal tip (172) is dome shaped. In some other versions, distal tip (172) is enlarged (e.g., configured as a ball tip or blueberry tip, etc.). The malleability of guide rail (170) allows guide rail (170) to be bent to a desired bend angle before being inserted into the head (H) of the patient (P). The malleability of guide rail (170) may allow guide rail (170) to maintain the bend angle while guide rail (170) is disposed in the head (H) of the patient (P), including while dilation catheter (160) is advanced distally relative to guide rail (170). Such operability of guide rail (170) may promote access by dilation catheter (160) to various locations within the head (H) of a patient (P), such as the maxillary sinus ostium, the frontal recess, the sphenoid sinus ostium, the Eustachian tube, etc., based on the selected bend angle. By way of example only, the bending of guide rail (170) may be performed in accordance with at least some of the teachings of U.S. Pat. No. 11,013,897, entitled "Apparatus for Bending Malleable Guide of Surgical Instrument," issued May 25, 2021, the disclosure of which is incorporated by reference herein, in its entirety. Guide rail (170) defines an inner lumen, in which guide element (180) is slidably disposed.

While instrument (100) of the present example includes guide rail (170) some other versions may include a guide catheter instead of including guide rail (170). Such a guide catheter may be positioned externally (yet still coaxially) relative to dilation catheter (160). Such a guide catheter may also effectively guide dilation catheter (160) into the targeted anatomical passageway. Such a guide catheter may be rigid or malleable. It should be understood that the teachings herein are not necessarily limited to the context of a guide rail (170), such that the teachings herein may be applied to other variations that include a guide catheter instead of including guide rail (170).

Dilation catheter (160) of the present example includes a first shaft (162) having an integral balloon (164) and a distal tip (166). First shaft (162) is coaxially positioned with outer sheath (152), guide rail (170), and guide element (180). First shaft (162) defines two inner lumens, including a first lumen in which guide rail (170) is slidably disposed and a second lumen in fluid communication with balloon (164). A manifold body (169) is secured to the proximal end of first shaft (162) and is further coupled with a second shaft (168). Second shaft (168) is laterally offset from first shaft (162) and defines an inner lumen that is in fluid communication with the second lumen of first shaft (162) via manifold body (169). The proximal end of second shaft (168) may thus be coupled with a source of fluid (e.g., saline, etc.), which may be used to selectively inflate balloon (164). Balloon (164) may comprise a non-extensible material and may be sized and configured to fit within a targeted anatomical passageway while in the deflated state; then dilate the targeted anatomical passageway while in the inflated state. It should be understood that balloon (164) is shown as being inflated in FIGS. 2A-2B, 3B, 2D, 3D, and 2E for schematic purposes only; and that balloon (164) may in fact be deflated at such stages of operation.

Guide element (180) of the present example comprises a shaft (182) having a distal tip (184). By way of example only, shaft (182) may comprise a polymeric material, a metallic material, a tubular structure, a helical structure (e.g., similar to a guidewire, etc.), and/or any other suitable material(s) or configuration(s). As best seen in FIGS. 3A-3E, an indicator element (186) is positioned at distal tip (184) of guide element (180). Indicator element (186) is configured to indicate the position of distal tip (184) in three-dimensional space.

In some versions, indicator element (186) comprises one or more position sensors. For instance, indicator element (186) may comprise one or more coils that generate signals in response to electromagnetic fields emitted by magnetic field generators (64), and processor (52) is operable to determine the real-time position of distal tip (184) in three-dimensional space based on the signals generated by indicator element (186). In such versions, one or more wires, conductive traces, or other electrically conductive elements may extend from indicator element (186) along at least part of the length of guide element (180). Signals from indicator element (186) may be communicated to processor (52) via wire or wirelessly.

In addition to comprising a position sensor, or in lieu of comprising a position sensor, indicator element (186) may comprise an illuminating feature that is operable to project light outwardly from indicator element (186). Such an illuminating feature may provide transillumination through the skin of the patient as described above. In some such versions, indicator element (186) includes an optically transmissive window that is optically coupled with one or more optical fibers, with such one or more optical fibers extending along at least part of the length of guide element (180) to a light source. In some other versions, indicator element (186) includes one or more LEDs or other local sources of light. In some such versions, one or more wires, conductive traces, or other electrically conductive elements may extend from indicator element (186) along at least part of the length of guide element (180) to a source of electrical power. It should be understood that indicator element (186) may comprise a position sensor, an illuminating feature, or a combination of a position sensor and an illuminating feature.

Figure 2A:
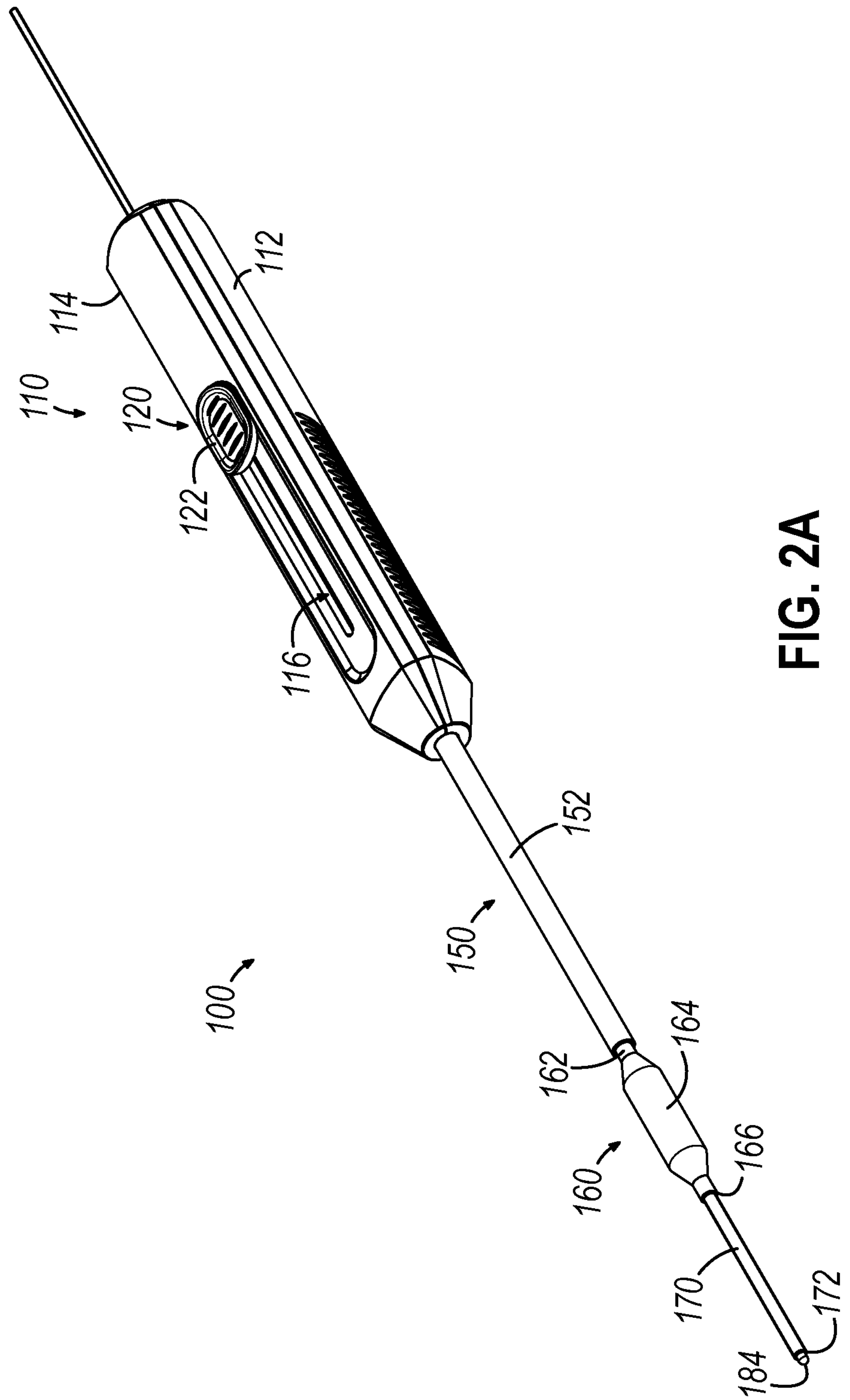
FIG. 2A depicts a perspective view of an example of a dilation instrument, with a dilation catheter in a proximal position.
Figure 3A:
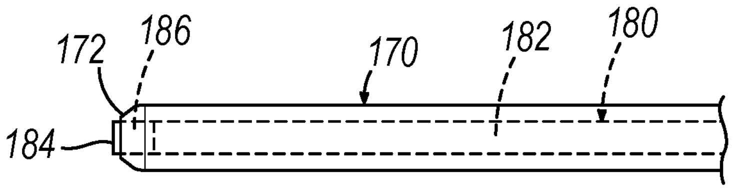
FIG. 3A depicts a side elevation view of a distal portion of a shaft assembly of the dilation instrument of FIG. 2A, with the dilation catheter in the proximal position.

FIGS. 2A and 3A show instrument (100) in an initial stage of operation, where dilation catheter (160) is in a proximal position. In this state, distal tip (184) of guide element (180) is positioned at distal tip (172) of guide rail (170). Also in this state, distal end distal tip (166) of dilation catheter (160) is spaced proximally from distal tips (172, 184). Thus, a distal region of guide rail (170) is exposed relative to dilation catheter (160). While guide rail (170) is shown in a straight configuration in FIGS. 2A and 3A, guide rail (170) may alternatively be in a bent configuration as noted above. The operator may select and execute the desired bend angle in guide rail (170) based on the location and/or configuration of the targeted anatomical passageway. Shaft assembly (150) may be inserted into the patient (P) while dilation catheter (160) is in the proximal position shown in FIGS. 2A and 3A. With distal tip (184) of guide element (180) is positioned at distal tip (172) of guide rail (170), the real-time position feedback provided by indicator element (186) may effectively indicate the real-time position of distal tip (172) in three-dimensional space.

Figure 2B:
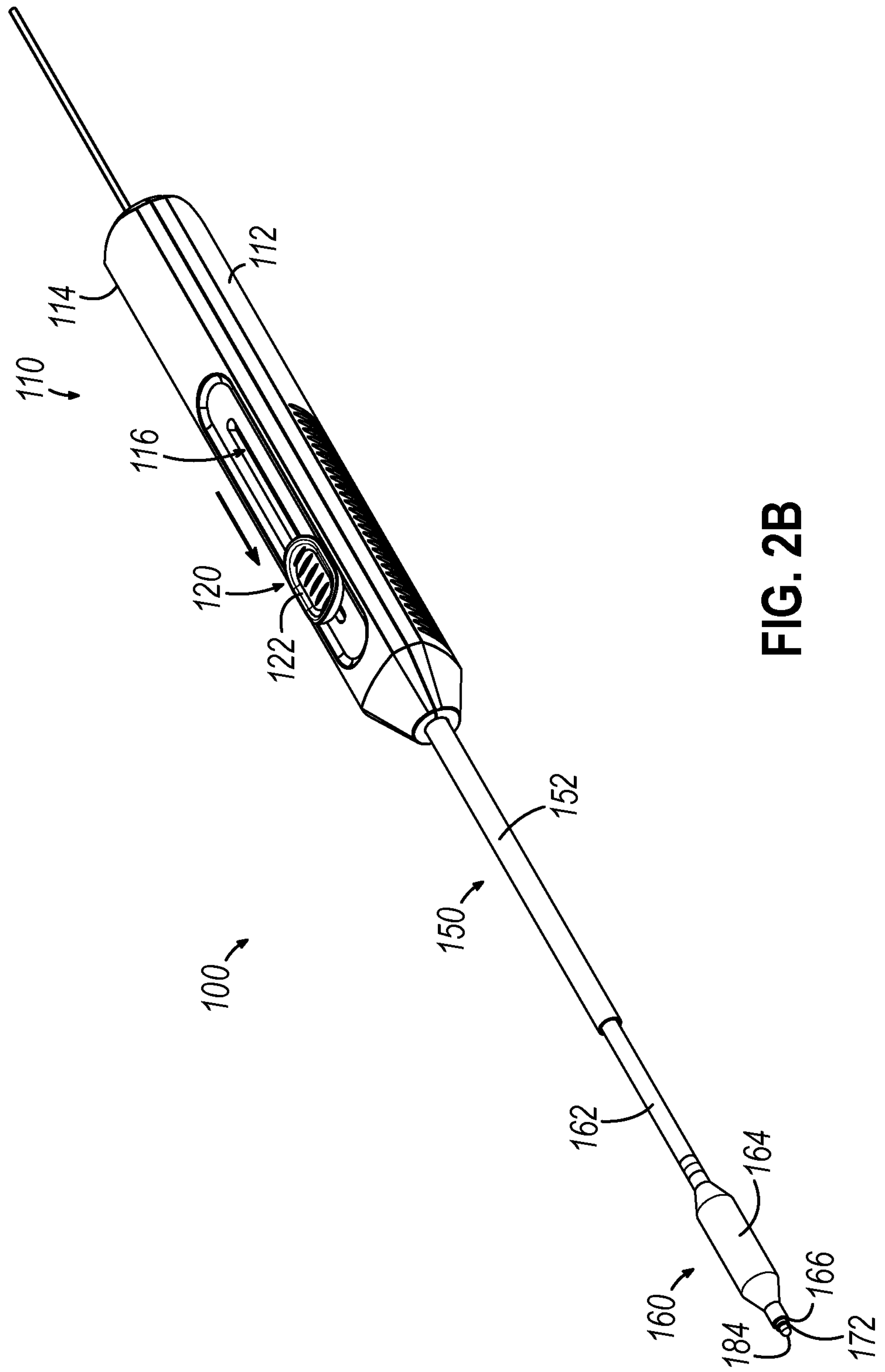
FIG. 2B depicts a perspective view of the dilation instrument of FIG. 2A, with the dilation catheter at an intermediate longitudinal position en route from the proximal position of FIG. 2A to a distal position.
Figure 2C:
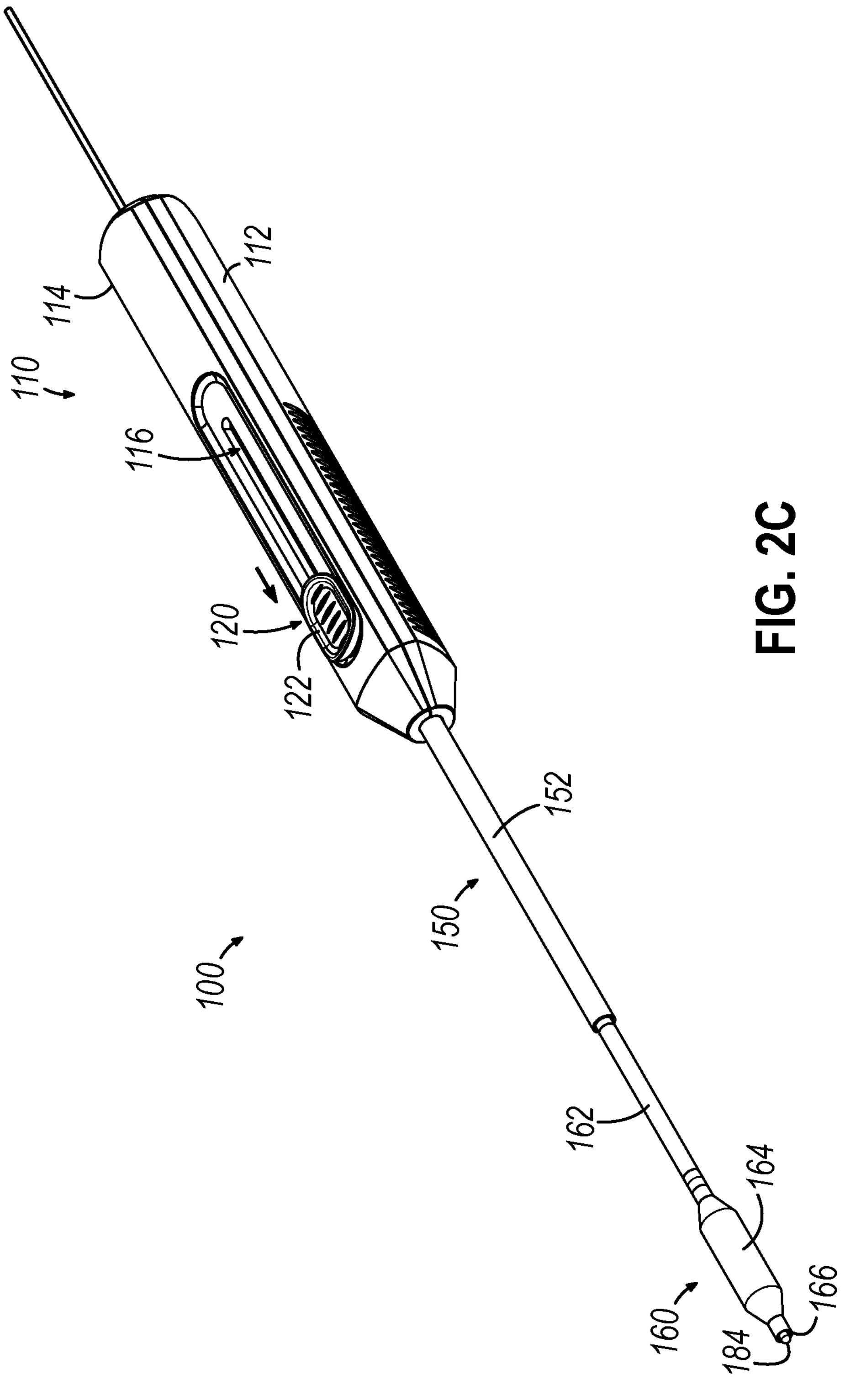
FIG. 2C depicts a perspective view of the dilation instrument of FIG. 2A, with the dilation catheter at the distal position.
Figure 3B:
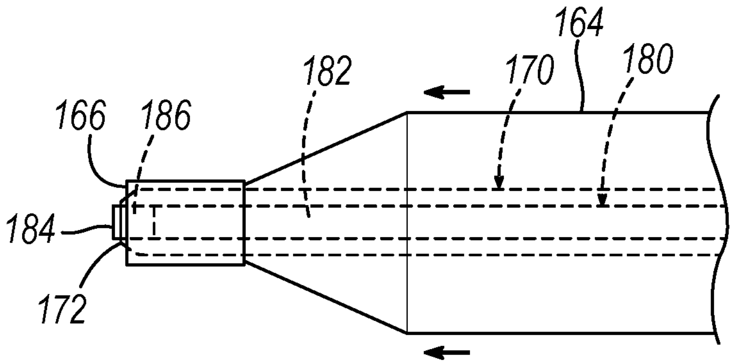
FIG. 3B depicts a side elevation view of the distal portion of the shaft assembly of FIG. 3A, with the dilation catheter at the intermediate longitudinal position of FIG. 2B, en route from the proximal position of FIG. 2A to the distal position of FIG. 2C.

Once the operator has sufficiently positioned distal tip (172) at the desired location, based on feedback from indicator element (186), the operator may begin advancing dilation catheter actuator (120) distally relative to housings (112, 114) as shown in FIGS. 2B-2C. This distal advancement of dilation catheter actuator (120) drives dilation catheter (160) distally as shown in FIGS. 2B-2C and 3B-3C. During the distal range of travel of dilation catheter (160), distal tip (166) eventually reaches the same longitudinal position of distal tips (172, 184), as shown in FIGS. 2B and 3B. As dilation catheter (160) continues to advance distally from that longitudinal position, guide element (180) translates distally with dilation catheter (160), maintaining distal tip (184) of guide element (180) at the same longitudinal position as distal tip (166) of dilation catheter (160). Thus, with distal tip (184) of guide element (180) positioned at distal tip (166) of dilation catheter (160), the real-time position feedback provided by indicator element (186) may effectively indicate the real-time position of distal tip (166) in three-dimensional space.

Figure 2D:
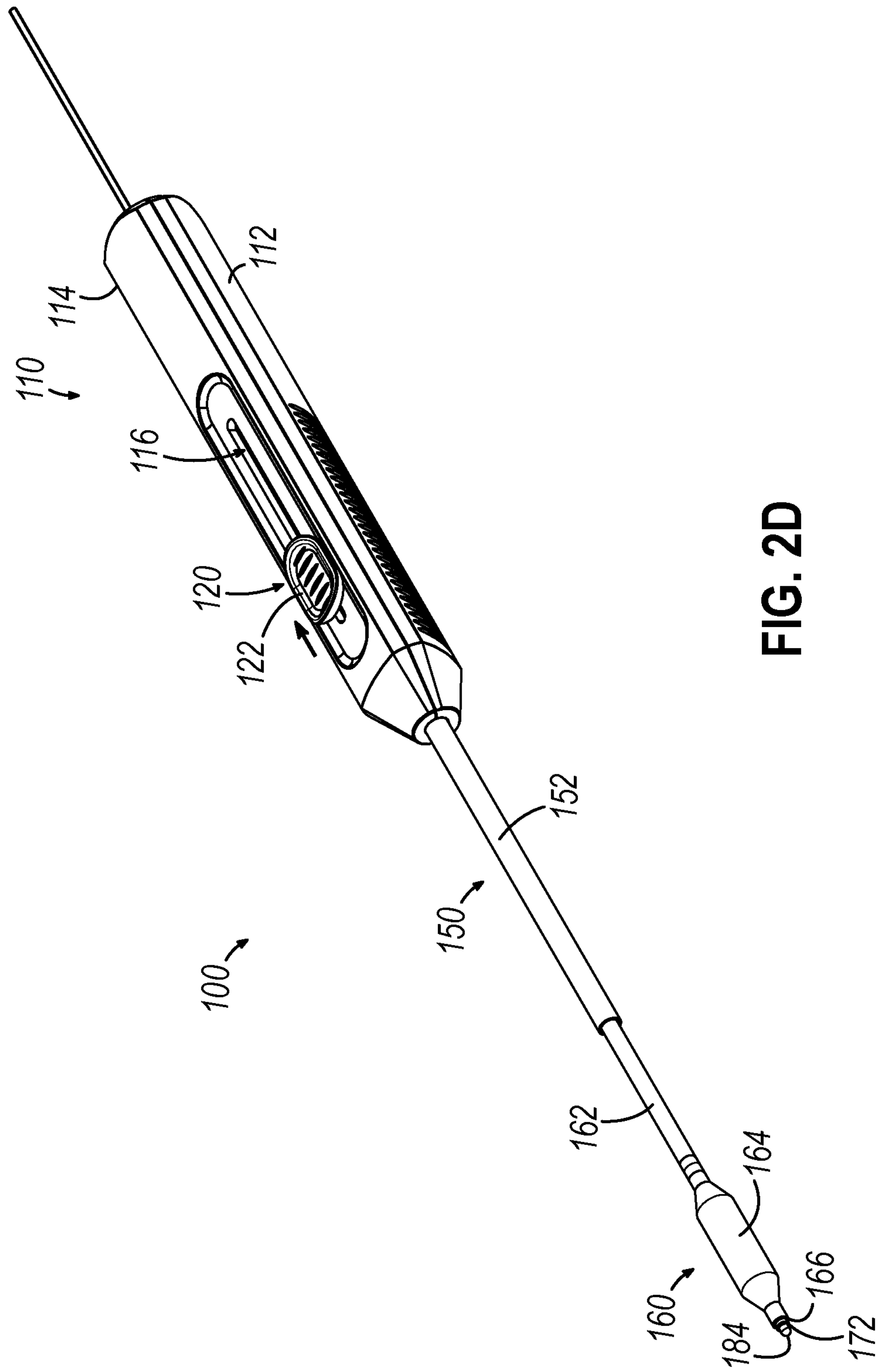
FIG. 2D depicts a perspective view of the dilation instrument of FIG. 2A, with the dilation catheter at an intermediate longitudinal position en route from the distal position of FIG. 2C to the proximal position of FIG. 2A.
Figure 2E:
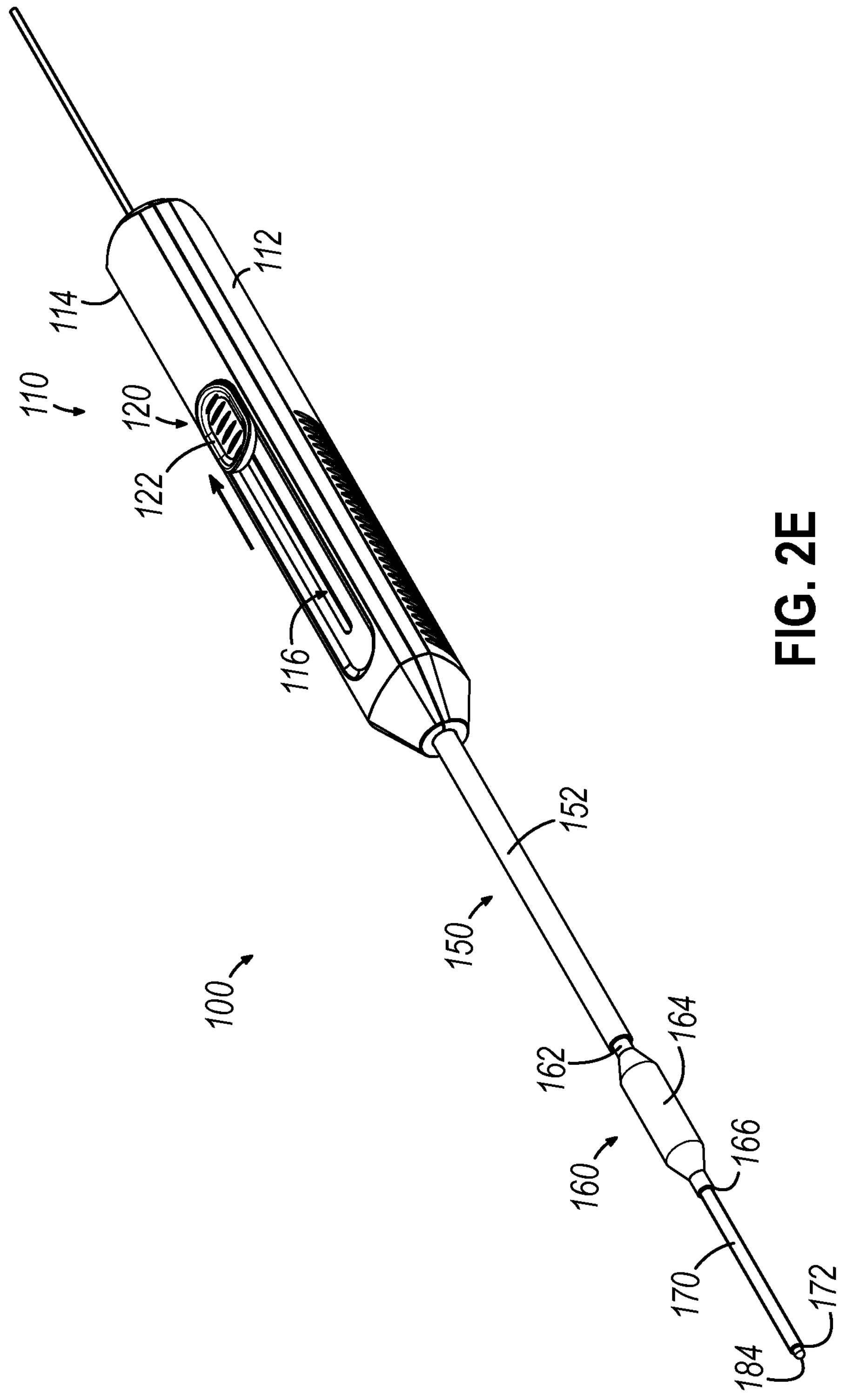
FIG. 2E depicts a perspective view of the dilation instrument of FIG. 2A, with the dilation catheter returned to the proximal position of FIG. 2A from the intermediate longitudinal position of FIG. 2D.
Figure 3C:
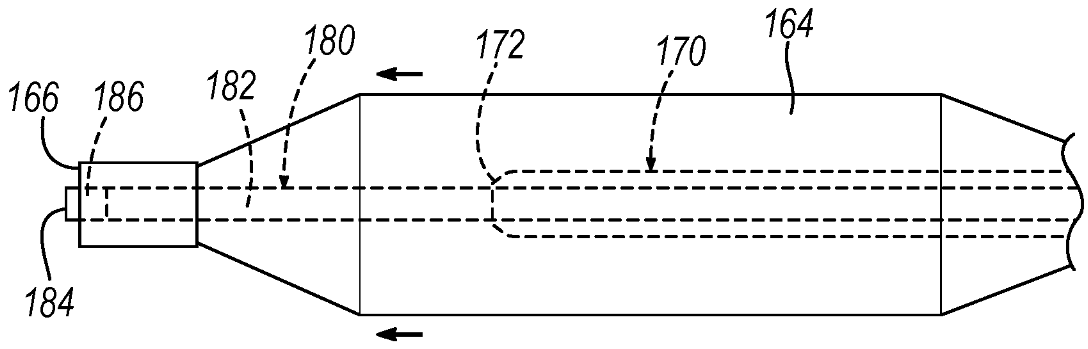
FIG. 3C depicts a side elevation view of the distal portion of the shaft assembly of FIG. 3A, with the dilation catheter at the distal position of FIG. 2C.

After reaching the distal position shown in FIGS. 2C and 3C, the operator may inflate balloon (164) to dilate the targeted anatomical passageway. In some cases, balloon (164) may be inflated and deflated repeatedly to achieve sufficient dilation. When the dilation is complete, balloon (164) may be deflated and retracted proximally as shown in the transition from FIGS. 2C and 3C to FIGS. 2D and 3D. As shown, dilation catheter (160) eventually reaches the position where distal tip (166) reaches the same longitudinal position of distal tips (172, 184). At this point, guide element (180) ceases further proximal movement while dilation catheter (160) continues to translate proximally, such that distal tip (184) of guide element (180) remains at distal tip (172) of guide rail (170) as shown in FIGS. 2E and 3E.

In view of the foregoing, during the stage of operation between that shown in FIGS. 2A and 3A and that shown in FIGS. 2B and 3B, the real-time position feedback provided by indicator element (186) may effectively indicate the real-time position of distal tip (172) in three-dimensional space. During the stage of operation between that shown in FIGS. 2B and 3B and that shown in FIGS. 2C and 3C, the real-time position feedback provided by indicator element (186) may effectively indicate the real-time position of distal tip (166) in three-dimensional space. During the stage of operation between that shown in FIGS. 2C and 3C and that shown in FIGS. 2D and 3D, the real-time position feedback provided by indicator element (186) may continue to effectively indicate the real-time position of distal tip (166) in three-dimensional space. During the stage of operation between that shown in FIGS. 2D and 3D and that shown in FIGS. 2E and 3E, the real-time position feedback provided by indicator element (186) may again effectively indicate the real-time position of distal tip (172) in three-dimensional space.

Figure 5:
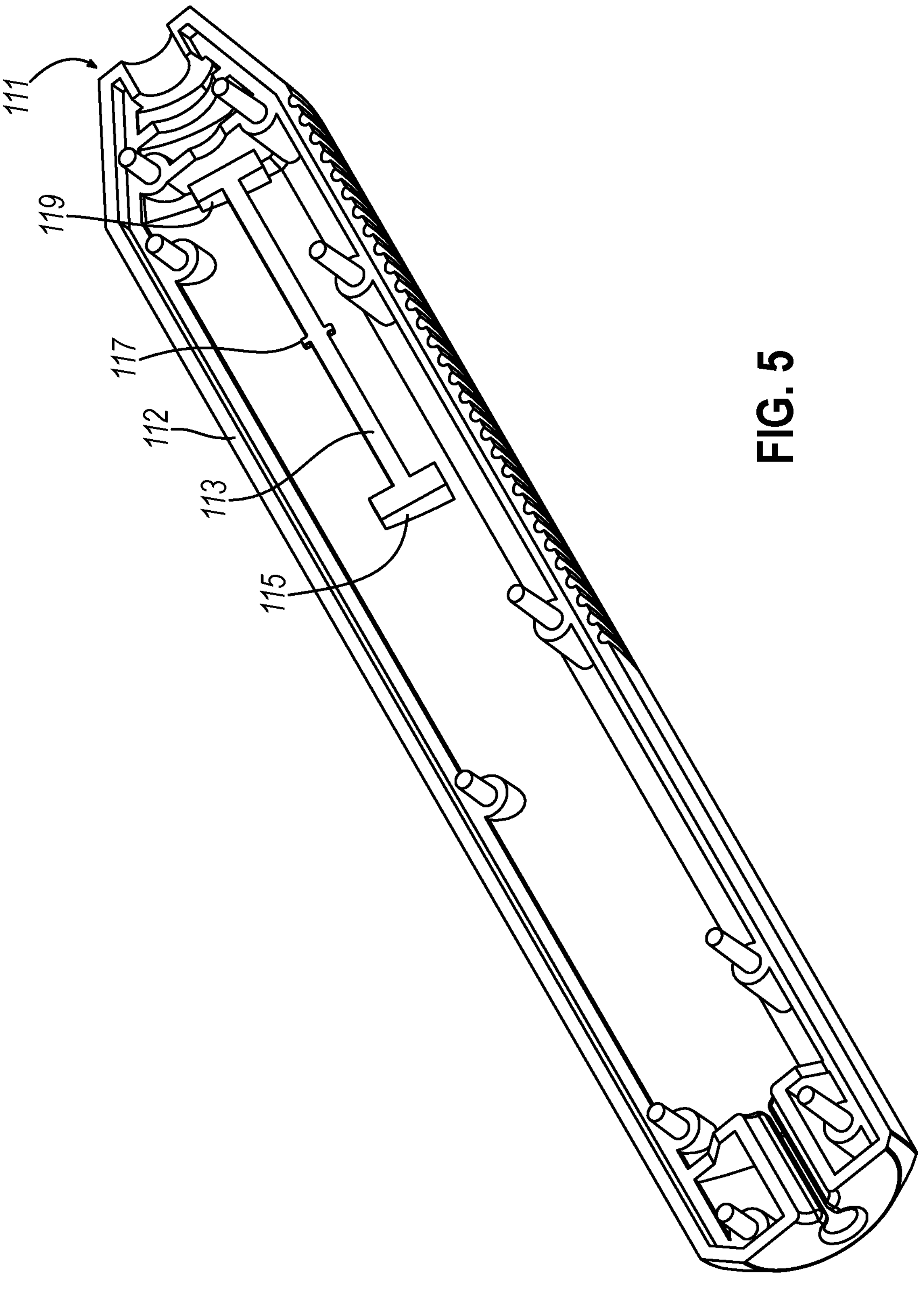
FIG. 5 depicts a perspective view of a housing of a body assembly of the dilation instrument of FIG. 2A.

FIGS. 5-9 show components of instrument (100) that provide the different spatial relationships during different stages of operation described above with reference to FIGS. 2A-2E and 3A-3E. In particular, FIG. 5 shows an interior region of first housing (112). As shown, first housing (112) defines an integral rail (113) extending between a proximal boss (115) and a distal boss (119), with a detent feature (117) positioned at an intermediate region along rail (113) between bosses (115, 119). Rail (113) and bosses (115, 119) are positioned near distal end (111) of first housing (112). Shaft assembly (150) extends distally from first housing (112) at distal end (111).

Figure 6:
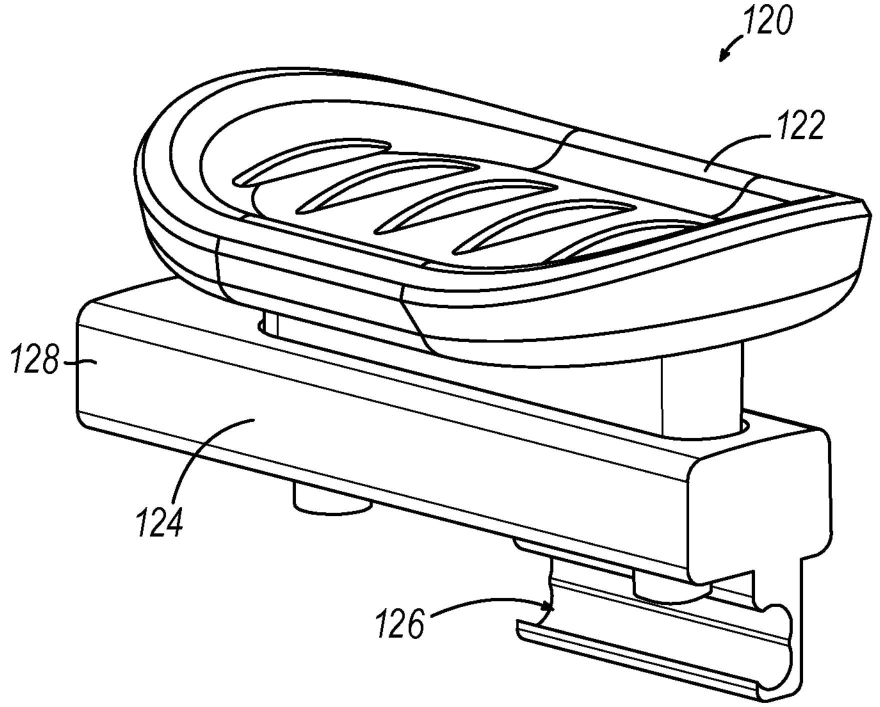
FIG. 6 depicts a perspective view of a dilation catheter actuator of the dilation instrument of FIG. 2A.
Figure 7:
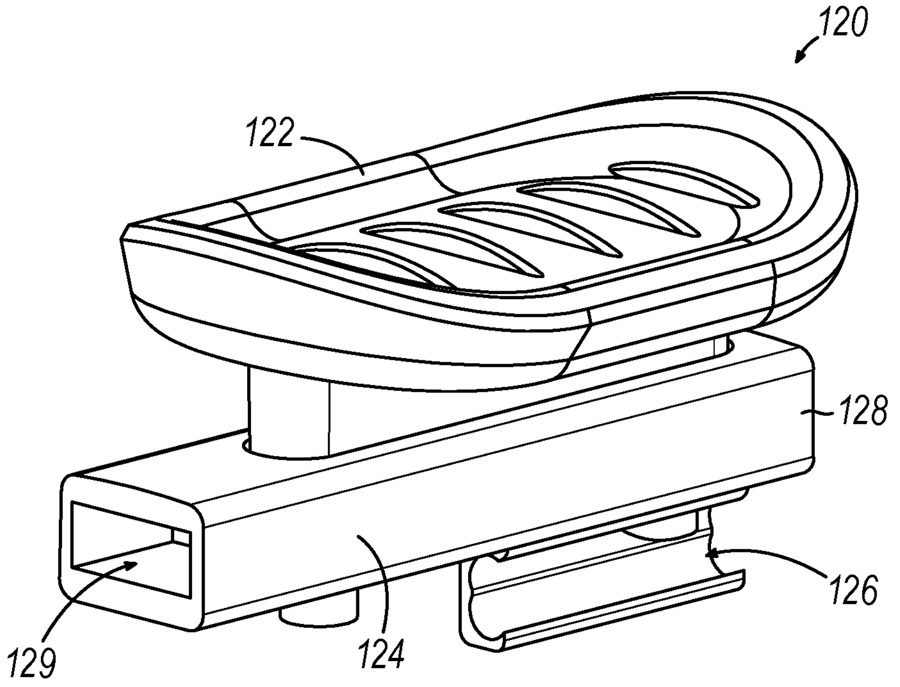
FIG. 7 depicts another perspective view of the dilation catheter actuator of FIG. 6.

FIGS. 6-7 show dilation catheter actuator (120) in greater detail. As shown, dilation catheter actuator (120) includes a finger pad (122), a body (124), and a shaft mount (126). Finger pad (122) is positioned outside of housings (112, 114) and is configured for engagement by the finger or thumb of the operator. Body (124) is positioned in the interior defined by housings (112, 114). Body (124) has a distal end (128) that defines an engagement recess (129) as will be described in greater detail below. Shaft mount (126) is configured to be fixedly coupled with second shaft (168) of dilation catheter (160), such that dilation catheter (160) translates longitudinally with dilation catheter actuator (120) relative to housings (112, 114). In some versions, shaft mount (126) is also configured to slidably accommodate a portion of guide rail (170), such that dilation catheter actuator (120) is configured to translate along guide rail (170).

Figure 8:
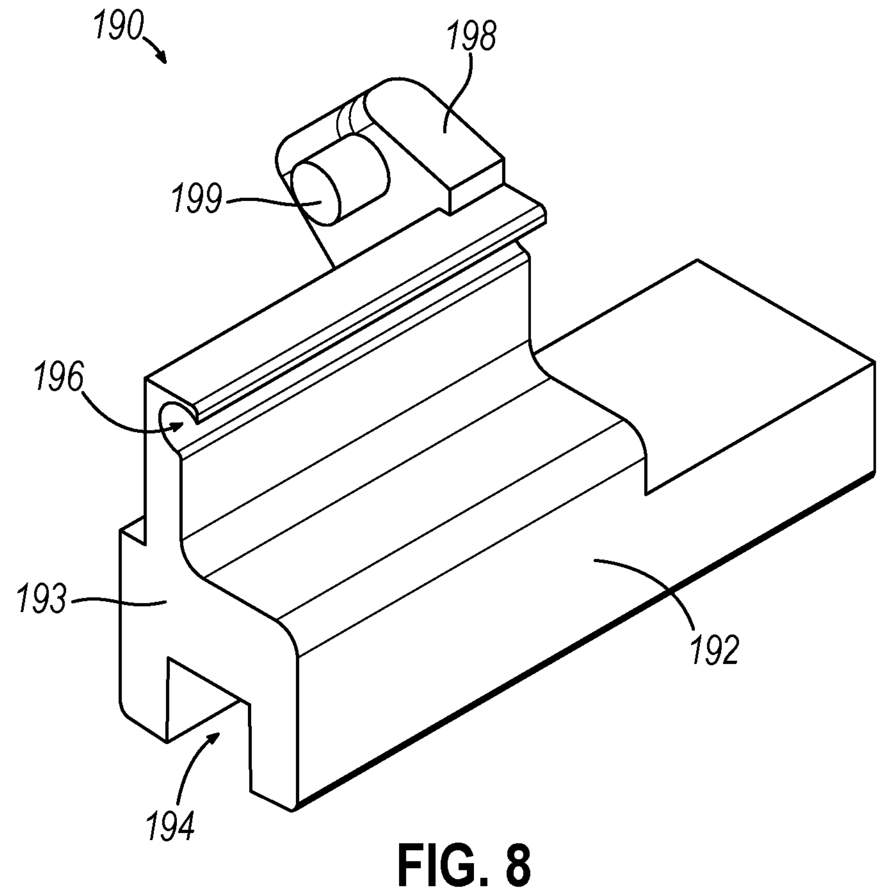
FIG. 8 depicts a perspective view of a guide element actuator of the dilation instrument of FIG. 2A.
Figure 9:
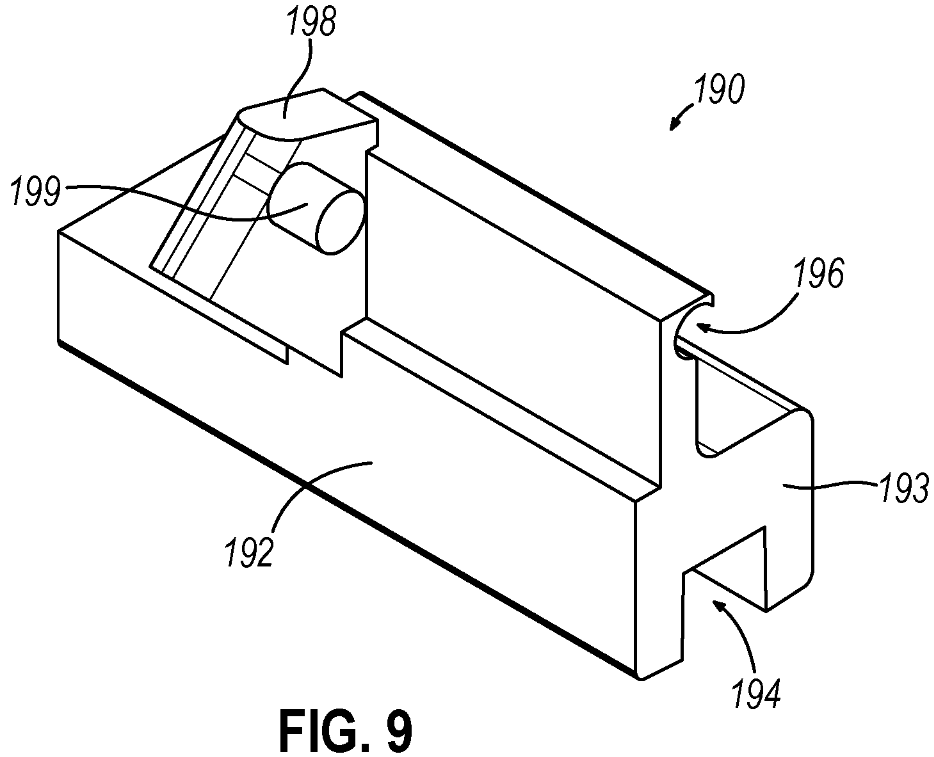
FIG. 9 depicts another perspective view of the guide element actuator of FIG. 8.

FIGS. 8-9 show a guide element actuator (190). Guide element actuator (190) comprises a body (192) having a proximal end (193) and a recess (194). Recess (194) is configured to receive rail (113) of first housing (112), such that guide element actuator (190) is slidable along rail (113). Guide element actuator (190) further includes a shaft mount (196), a flange (198) extending laterally relative to body (192), and an engagement peg (199) extending proximally from flange (198). Peg (199) is sized and configured to enter engagement recess (129) with a friction fit, as will be described in greater detail below. In the present example, peg (199) has a cylindrical configuration. In some other versions, peg (199) has a frusto-conical configuration or some other configuration. Recess (129) may also have any suitable configuration and/or friction promoting features (e.g., elastomeric material, internal ridges or knurling, etc.). While only one peg (199) is shown, guide element actuator (190) may have any other suitable number of pegs (199). Shaft mount (196) is configured to be fixedly coupled with guide element (180), such that guide element (180) translates longitudinally with guide element actuator (190) relative to housings (112, 114).

FIGS. 10A-10E show engagement between first housing (112), dilation catheter actuator (120), and guide element actuator (190) during the stages of operation described above with reference to FIGS. 2A-2E and 3A-3E. The stage of operation shown in FIG. 10A corresponds with the stage of operation shown in FIGS. 2A and 3A. At this stage, dilation catheter actuator (120) is in a proximal position, such that distal end (128) of body (124) is spaced proximally from flange (198) of guide element actuator (190). Proximal end (193) of body (192) abuts proximal boss (115) of first housing (112). Body (192) is proximal to detent (117) along rail (113) of first housing (112). In some cases, engagement between body (192) and detent (117) may prevent premature or otherwise undesired distal advancement of guide element actuator (190) relative to housings (112, 114).

Figure 10A:
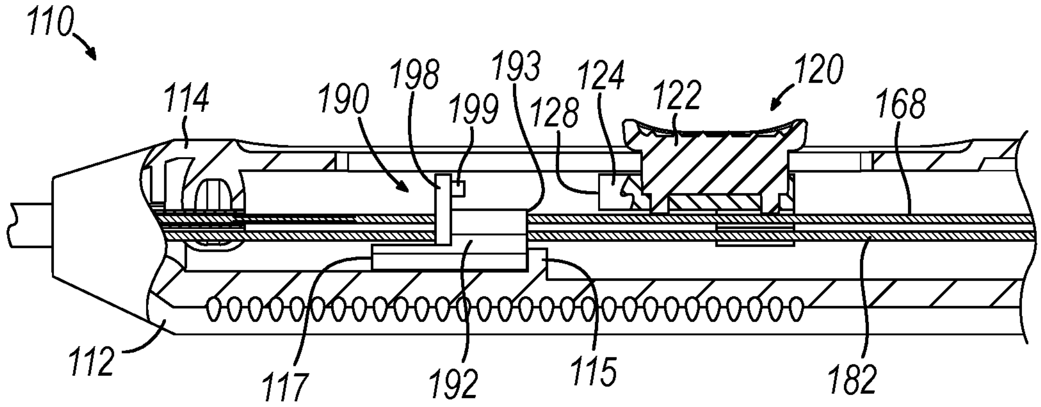
FIG. 10A depicts a cross-sectional side view of the body assembly of the dilation instrument of FIG. 2A, with the dilation catheter in the proximal position of FIG. 2A.
Figure 10B:
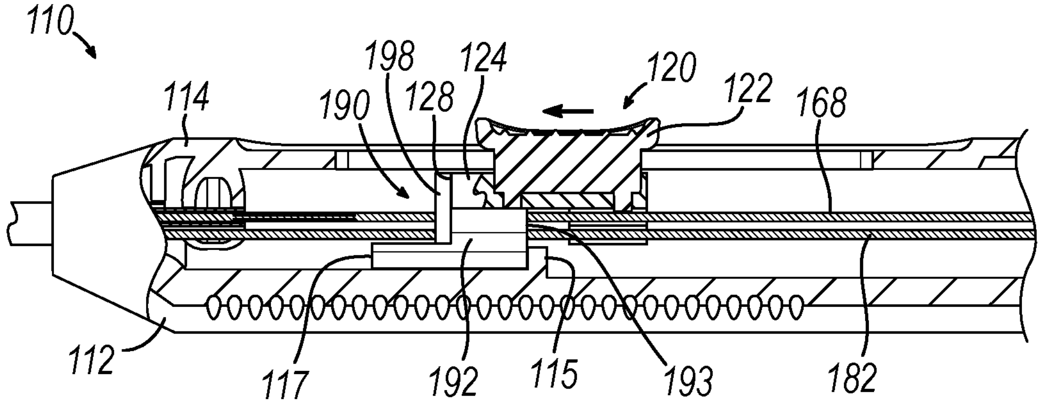
FIG. 10B depicts a cross-sectional side view of the body assembly of the dilation instrument of FIG. 2A, with the dilation catheter at the intermediate longitudinal position of FIG. 2B, en route from the proximal position of FIG. 2A to the distal position of FIG. 2C.

The stage of operation shown in FIG. 10B corresponds with the stage of operation shown in FIGS. 2B and 3B. At this stage of operation, dilation catheter actuator (120) is advanced to a position where distal end (128) of body (124) engages flange (198) of guide element actuator (190); and such that peg (199) enters engagement recess (129). In some cases, peg (199) is not yet fully seated into engagement recess (129) at this stage of operation. In the example shown in FIG. 10B, proximal end (193) of body (192) continues to abut proximal boss (115) of first housing (112) at this stage of operation.

Figure 10C:
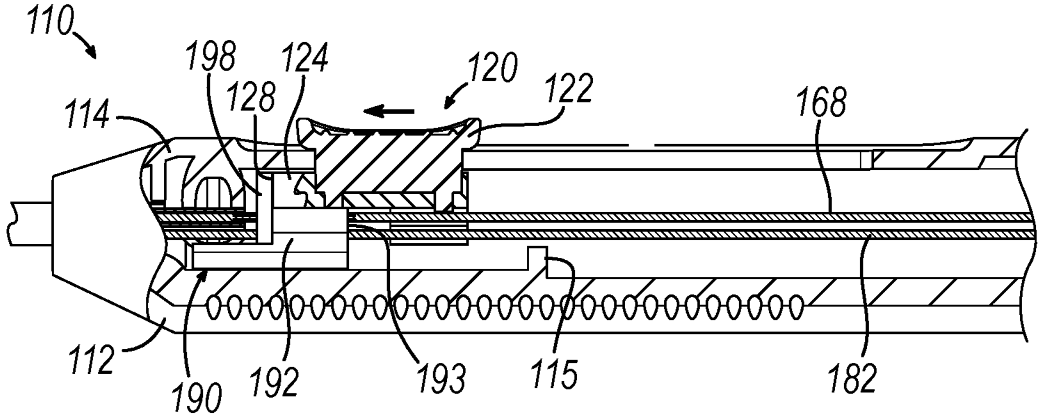
FIG. 10C depicts a cross-sectional side view of the body assembly of the dilation instrument of FIG. 2A, with the dilation catheter at the distal position of FIG. 2C.

The stage of operation shown in FIG. 10C corresponds with the stage of operation shown in FIGS. 2C and 3C. At this stage of operation, dilation catheter actuator (120) is advanced to the distal-most position; and has pushed guide element actuator (190) to a distal-most position through engagement between distal end (128) of body (124) and flange (198) of guide element actuator (190). In some scenarios, body (192) abuts distal boss (119) of first housing (112) at this stage of operation. In some such scenarios, and to the extent that peg (199) was not yet fully seated into engagement recess (129) after reaching the stage shown in FIG. 10B, distal boss (119) may provide a mechanical ground for guide element actuator (190) that promotes full seating of peg (199) into engagement recess (129) as dilation catheter actuator (120) is urged distally. With peg (199) fully seated in engagement recess (129), guide element actuator (190) and dilation catheter actuator are coupled together through a friction fit.

Figure 3D:
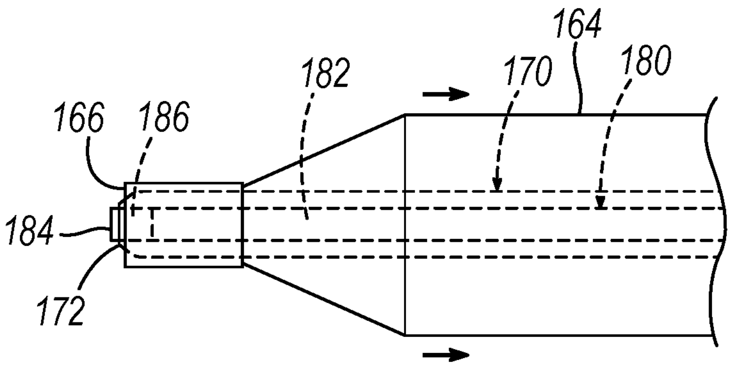
FIG. 3D depicts a side elevation view of the distal portion of the shaft assembly of FIG. 3A, with the dilation catheter at the intermediate longitudinal position of FIG. 2D, en route from the distal position of FIG. 2C to the proximal position of FIG. 2A.
Figure 3E:
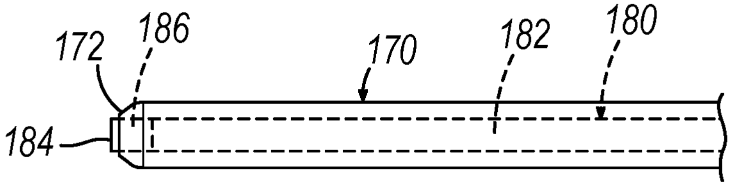
FIG. 3E depicts a side elevation view of the distal portion of the shaft assembly of FIG. 3A, with the dilation catheter returned to the proximal position of FIG. 2A from the intermediate longitudinal position of FIG. 2D.
Figure 10D:
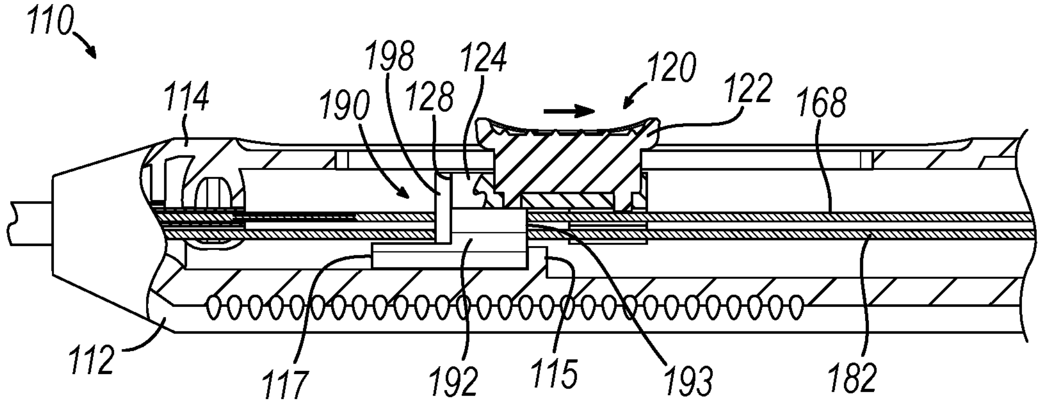
FIG. 10D depicts a cross-sectional side view of the body assembly of the dilation instrument of FIG. 2A, with the dilation catheter at the intermediate longitudinal position of FIG. 2D, en route from the distal position of FIG. 2C to the proximal position of FIG. 2A.

The stage of operation shown in FIG. 10D corresponds with the stage of operation shown in FIGS. 2D and 3D. At this stage of operation, the operator has begun driving dilation catheter actuator (120) back toward the proximal position. As shown, due to the friction fit of peg (199) in engagement recess (129), dilation catheter actuator (120) pulls guide element actuator (190) proximally from the position shown in FIG. 10C to the position shown in FIG. 10D. In the present example, the friction fit of peg (199) in engagement recess (129) is sufficient to overcome any resistance provided by detent (117) as guide element actuator (190) travels from the position shown in FIG. 10C to the position shown in FIG. 10D, such that the resistance imparted by detent (117) on body (192) does not cause dilation catheter actuator (120) to decouple from guide element actuator (190). Upon reaching the position shown in FIG. 10D, proximal end (193) of body (192) again abuts proximal boss (115) of first housing (112). This engagement between proximal end (193) of body (192) and proximal boss (115) of first housing (112) prevents further proximal movement of guide element actuator (190) relative to first housing (112).

Figure 10E:
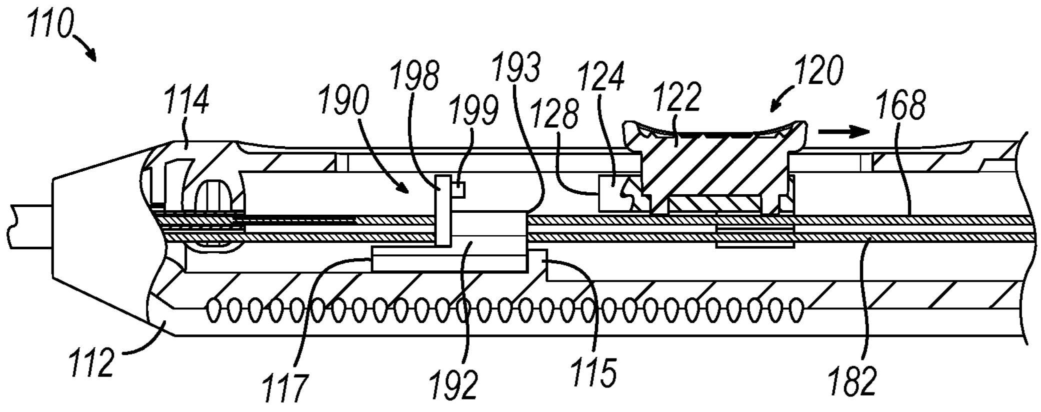
FIG. 10E depicts a cross-sectional side view of the body assembly of the dilation instrument of FIG. 2A, with the dilation catheter returned to the proximal position of FIG. 2A from the intermediate longitudinal position of FIG. 2D.

The stage of operation shown in FIG. 10E corresponds with the stage of operation shown in FIGS. 2E and 3E. At this stage of operation, the operator has driven dilation catheter actuator (120) further back to the proximal position. As the operator urges dilation catheter actuator (120) proximally from the position shown in FIG. 10D to the position shown in FIG. 10E, peg (199) disengages from engagement recess (129), due to the arresting engagement between proximal end (193) of body (192) and proximal boss (115) of first housing (112).

Figure 11:
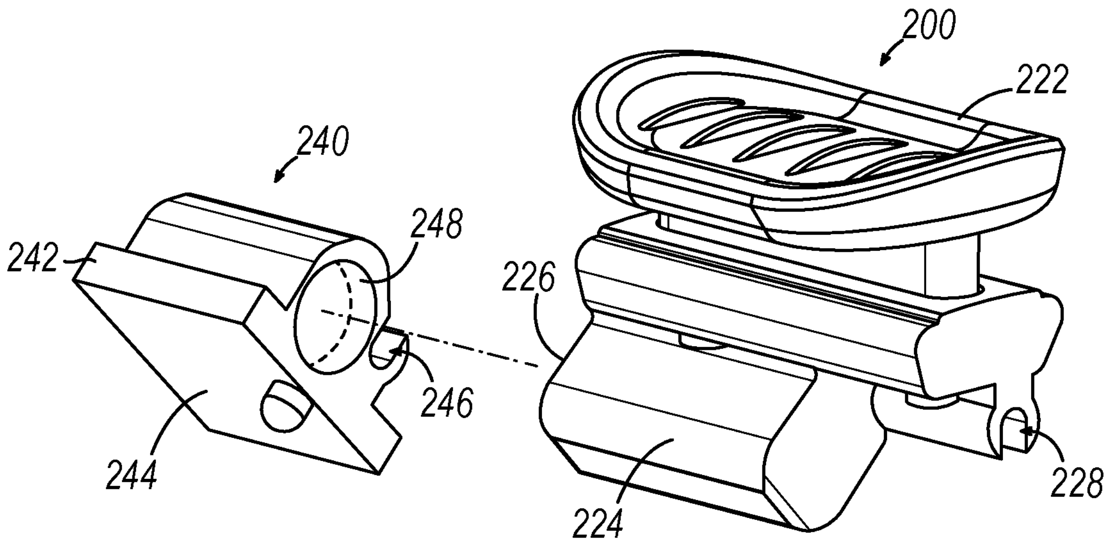
FIG. 11 depicts a perspective view of an example of an alternative dilation catheter actuator and guide element actuator that may be integrated into the dilation instrument of FIG. 2A.
Figure 12:
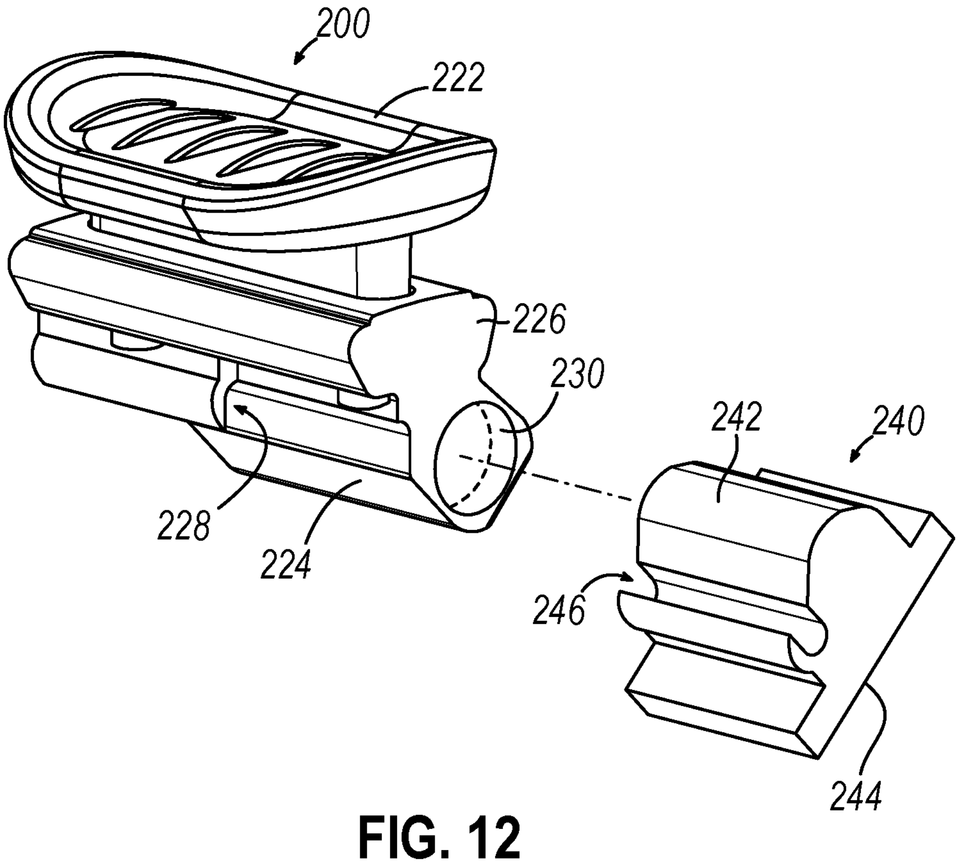
FIG. 12 depicts another perspective view of the dilation catheter actuator and guide element actuator of FIG. 11.

B. Example of Magnetically Coupled Interlocking Dilation Catheter Actuator and Guide Element Actuator for Dilation Instrument While instrument (100) utilizes a friction fit between peg (199) and engagement recess (129) to removably couple guide element actuator (190) with dilation catheter actuator (120), it may be desirable to provide an alternative form of removable coupling between guide element actuator (190) and dilation catheter actuator (120). One example of such an alternative is shown in FIGS. 11-12. In particular, FIGS. 11-12 show an alternative dilation catheter actuator (200) and an alternative guide element actuator (240) that may be integrated into a variation of instrument (100). Dilation catheter actuator (200) of this example includes a finger pad (222), a body (224), and a shaft mount (228). Finger pad (222) is configured to be positioned outside of housings (112, 114) and is configured for engagement by the finger or thumb of the operator. Body (224) is configured to be positioned in the interior defined by housings (112, 114). Body (224) has a distal end (226) that has a magnet (230) fixedly secured therein. Shaft mount (228) is configured to be fixedly coupled with second shaft (168) of dilation catheter (160), such that dilation catheter (160) translates longitudinally with dilation catheter actuator (220) relative to housings (112, 114). In some versions, shaft mount (228) is also configured to slidably accommodate a portion of guide rail (170), such that dilation catheter actuator (220) is configured to translate along guide rail (170).

Guide element actuator (240) comprises a body (242) having a proximal end (244) and a magnet (248) fixedly secured therein. Body (242) is configured to slidably engage a rail and/or other feature of one or both of housings (112, 114), such that body (242) may translate longitudinally relative to housings (112, 114) while still being supported relative to housings (112, 114). Guide element actuator (240) further includes a shaft mount (226). Shaft mount (226) is configured to be fixedly coupled with guide element (180), such that guide element (180) translates longitudinally with guide element actuator (240) relative to housings (112, 114).

Guide element actuator (240) and dilation catheter actuator (200) may cooperate with each other in a manner similar to guide element actuator (190) and dilation catheter actuator (120), except that magnets (230, 248) provide the removable coupling between guide element actuator (240) and dilation catheter actuator (200) instead of peg (199) and engagement recess (129). In particular, when dilation catheter actuator (200) is translated distally along a first range of motion (similar to what is shown in the transition from FIG. 2A to FIG. 2B and in the transition from FIG. 10A to FIG. 10B), dilation catheter (160) may advance distally while guide element (180) remains stationary (similar to what is shown in the transition from FIG. 2A to FIG. 2B and in the transition from FIG. 3A to FIG. 3B). As dilation catheter actuator (200) is translated further distally along a second range of motion (similar to what is shown in the transition from FIG. 2B to FIG. 2C and in the transition from FIG. 10B to FIG. 10C), dilation catheter actuator (200) engages guide element actuator (240) and drives guide element actuator (240) distally, thereby driving guide element (180) distally with dilation catheter (160) (similar to what is shown in the transition from FIG. 2B to FIG. 2C and in the transition from FIG. 3B to FIG. 3C).

When the operator retracts dilation catheter actuator (200) proximally along a first range of motion (similar to what is shown in the transition from FIG. 2C to FIG. 2D and in the transition from FIG. 10C to FIG. 10D), the magnetic coupling between magnets (230, 248) will cause dilation catheter actuator (200) to pull guide element actuator (240) proximally, thereby driving guide element (180) proximally with dilation catheter (160) (similar to what is shown in the transition from FIG. 2C to FIG. 2D and in the transition from FIG. 3C to FIG. 3D). As dilation catheter actuator (200) is translated further proximally along a second range of motion (similar to what is shown in the transition from FIG. 2D to FIG. 2E and in the transition from FIG. 10D to FIG. 10E), guide element actuator (240) engages proximal boss (115) of first housing (112) (or some other fixed structure within one or both of housings (112, 114)), such that proximal boss (115) arrests further proximal movement of guide element actuator (240) and guide element (180). The engagement between proximal end (244) and proximal boss (115) causes magnets (230, 248) to decouple, such that dilation catheter actuator (200) and dilation catheter (160) continue translating proximally while guide element actuator (240) and guide element (180) remain stationary (similar to what is shown in the transition from FIG. 2D to FIG. 2E and in the transition from FIG. 3D to FIG. 3E).

In the present example, dilation catheter actuator (200) and guide element actuator (240) each comprises a respective magnet (230, 248). In some other variations, one of magnets (230, 248) is substituted for a ferrous element. As another example of such a variation, body (226) or body (226) may be formed of a ferrous material, in lieu of containing a respective magnet (230, 248).

C. Example of Dilation Instrument with Resiliently Biased Interlocking of Dilation Catheter Actuator with Guide Element Actuator FIGS. 13A-13E show an example of an alternative dilation instrument (300). Instrument (300) of this example may be configured and operable like instrument (100) described above, except for the differences described below. Instrument (300) of this example includes a body assembly (310) and a shaft assembly (350), which may be configured and operable similar to a body assembly (110) and a shaft assembly (150) of instrument (100). Body assembly (310) includes an internal boss (312) and a dilation catheter actuator (320). Dilation catheter actuator (320) may be coupled with dilation catheter (160) similar to the coupling between dilation catheter actuator (120) and dilation catheter (160) as described above. A guide element actuator (330) is slidably disposed in body assembly (310); and may be coupled with guide element (180) similar to the coupling between guide element actuator (190) and guide element (180) as described above.

Dilation catheter actuator (320) of the present example includes a finger pad (322), a body (324), and a ball (326), which is resiliently biased downwardly by a spring (328). Finger pad (322) is positioned in an exterior region of body assembly (310) and is configured for engagement by the finger or thumb of the operator. Body (324) is positioned in an interior region of body assembly (310). Guide element actuator (330) defines an upwardly facing recess (332), which is configured to receive ball (326) as described in greater detail below.

Guide element actuator (330) and dilation catheter actuator (320) may cooperate with each other in a manner similar to guide element actuator (190) and dilation catheter actuator (120), except that ball (326) and recess (332) provide the removable coupling between guide element actuator (330) and dilation catheter actuator (320) instead of peg (199) and engagement recess (129). In particular, when dilation catheter actuator (320) is translated distally along a first range of motion as shown in the transition from FIG. 13A to FIG. 13B, dilation catheter (160) may advance distally while guide element (180) remains stationary (similar to what is shown in the transition from FIG. 2A to FIG. 2B and in the transition from FIG. 3A to FIG. 3B). During this transition, ball (326) may engage guide element actuator (330) and translate along guide element actuator (330), with spring (328) compressing, until ball (326) reaches recess (332). Upon ball (326) reaching recess (332), spring (328) urges ball (326) downwardly into recess (332), thereby removably coupling guide element actuator (330) with dilation catheter actuator (320). As dilation catheter actuator (320) is translated further distally along a second range of motion as shown in the transition from FIG. 13B to FIG. 13C, dilation catheter actuator (320) drives guide element actuator (330) distally due to the resilient engagement of ball (326) in recess (332), thereby driving guide element (180) distally with dilation catheter (160) (similar to what is shown in the transition from FIG. 2B to FIG. 2C and in the transition from FIG. 3B to FIG. 3C).

Figure 13A:
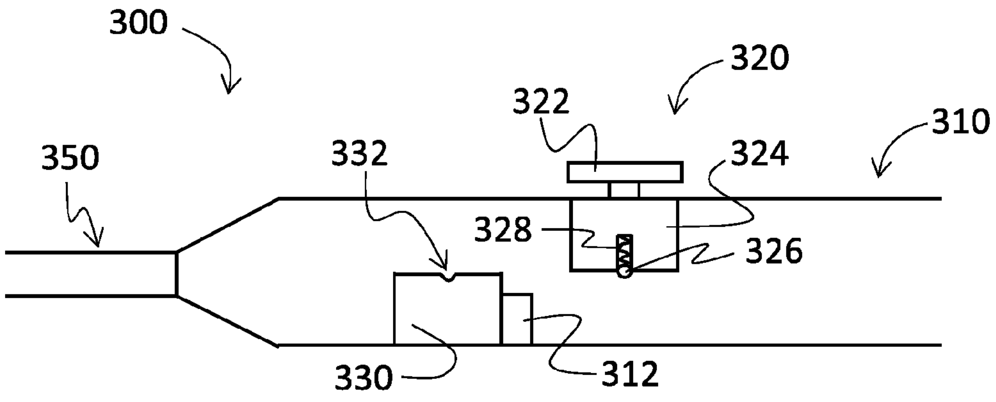
FIG. 13A depicts a schematic view of another example of a dilation instrument, with a dilation catheter actuator in a proximal position.
Figure 13B:
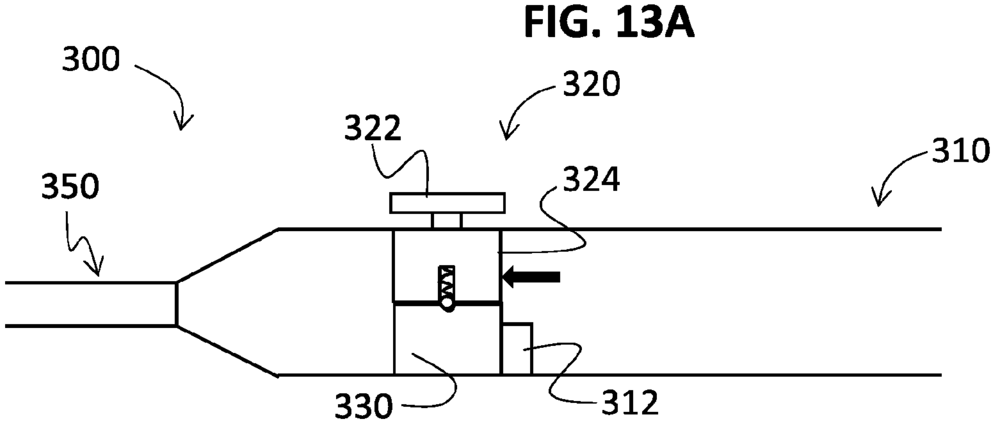
FIG. 13B depicts a schematic view of the dilation instrument of FIG. 13A, with the dilation catheter actuator at an intermediate longitudinal position en route from the proximal position of FIG. 13A to a distal position.
Figure 13C:
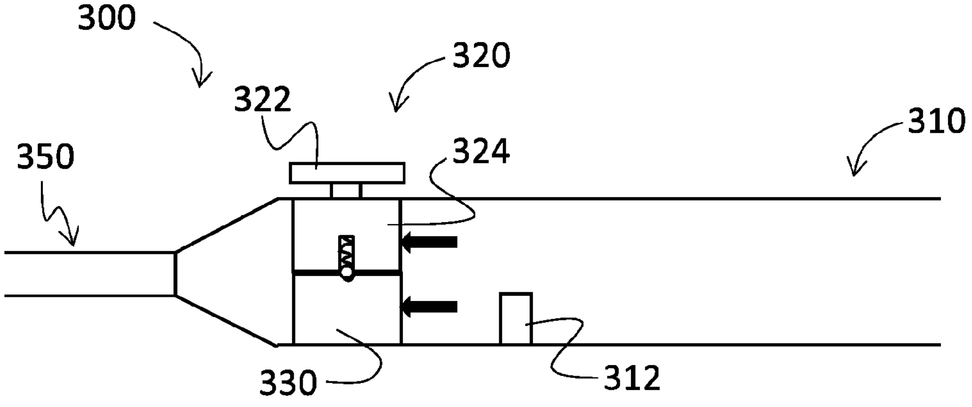
FIG. 13C depicts a schematic view of the dilation instrument of FIG. 13A, with the dilation catheter actuator at the distal position.
Figure 13D:
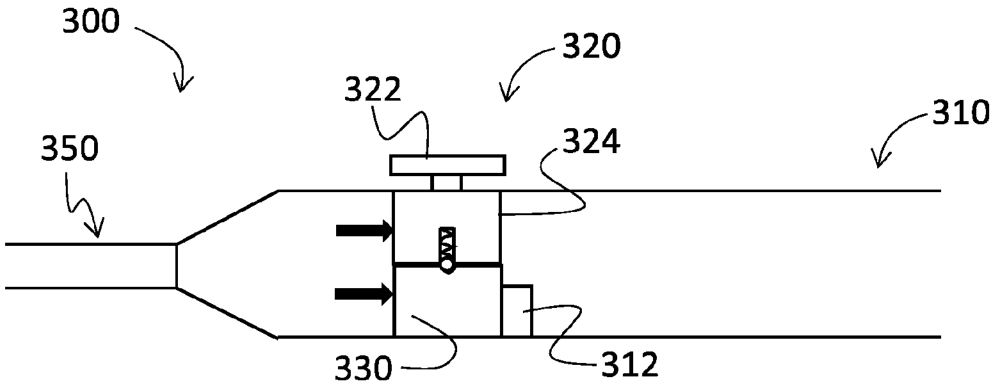
FIG. 13D depicts a schematic view of the dilation instrument of FIG. 13A, with the dilation catheter actuator at an intermediate longitudinal position en route from the distal position of FIG. 13C to the proximal position of FIG. 13A.
Figure 13E:
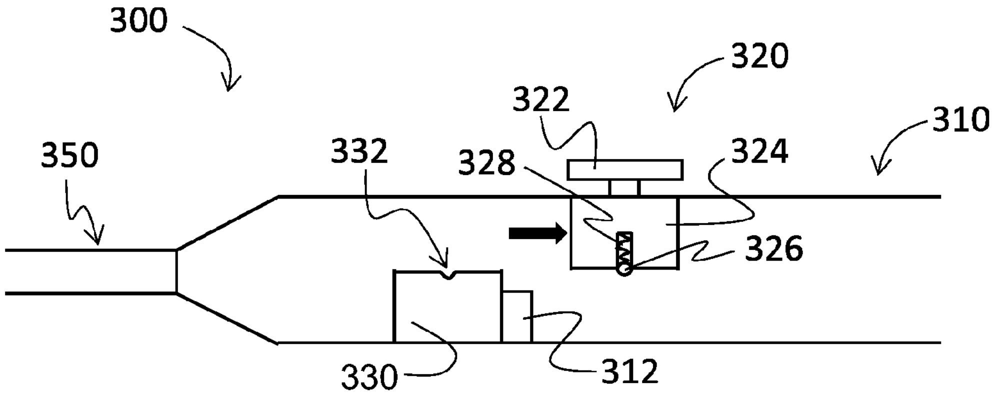
FIG. 13E depicts a schematic view of the dilation instrument of FIG. 13A, with the dilation catheter actuator returned to the proximal position of FIG. 13A from the intermediate longitudinal position of FIG. 13D.

When the operator retracts dilation catheter actuator (320) proximally along a first range of motion as shown the transition from FIG. 13C to FIG. 13D, the resilient engagement of ball (326) in recess (332) will cause dilation catheter actuator (320) to pull guide element actuator (330) proximally, thereby driving guide element (180) proximally with dilation catheter (160) (similar to what is shown in the transition from FIG. 2C to FIG. 2D and in the transition from FIG. 3C to FIG. 3D). As dilation catheter actuator (320) is translated further proximally along a second range of motion as shown in the transition from FIG. 13D to FIG. 13E, guide element actuator (330) engages internal boss (312), such that internal boss (312) arrests further proximal movement of guide element actuator (330) and guide element (180). The engagement between guide element actuator (330) and internal boss (312) causes ball (326) to disengage from recess (332), such that dilation catheter actuator (320) and dilation catheter (160) continue translating proximally while guide element actuator (330) and guide element (180) remain stationary (similar to what is shown in the transition from FIG. 2D to FIG. 2E and in the transition from FIG. 3D to FIG. 3E).

In the present example, dilation catheter actuator (320) and guide element actuator (330) are removably coupled through a resiliently biased feature in the form of a ball (326) that is resiliently urged by a spring (328). Alternatively, any other suitable kind of resilient member other than spring (328) may be used to resiliently bias ball (326) into engagement with recess (332). Similarly, any other suitable kind of resiliently biased structure other than ball (326) may be utilized to provide removable coupling between dilation catheter actuator (320) and guide element actuator (330). By way of example only, a cantilevered arm, latch, or other resilient feature may provide a removable coupling between dilation catheter actuator (320) and guide element actuator (330). In versions where the resilient feature comprises a cantilevered latch, the cantilevered latch may extend distally, proximally, or in any other suitable direction. Alternatively, the resilient feature may take any other suitable form. While the resilient feature is integrated into dilation catheter actuator (320) in this example, other variations may integrate a resilient feature into guide element actuator (330).

D. Example of Dilation Instrument with Dilation Catheter Actuator and Guide Element Actuator with Lost Motion FIGS. 14A-14E show another example of an alternative dilation instrument (400). Instrument (400) of this example may be configured and operable like instrument (100) described above, except for the differences described below. Instrument (400) of this example includes a body assembly (410) and a shaft assembly (450), which may be configured and operable similar to a body assembly (110) and a shaft assembly (150) of instrument (100). Body assembly (410) includes a dilation catheter actuator (420). Dilation catheter actuator (420) may be coupled with dilation catheter (160) similar to the coupling between dilation catheter actuator (120) and dilation catheter (160) as described above. A guide element actuator (430) is slidably disposed in body assembly (410); and may be coupled with guide element (180) similar to the coupling between guide element actuator (190) and guide element (180) as described above.

Dilation catheter actuator (420) of the present example includes a finger pad (422) and a body (424). Finger pad (422) is positioned in an exterior region of body assembly (410) and is configured for engagement by the finger or thumb of the operator. Body (424) is positioned in an interior region of body assembly (410). Guide element actuator (430) includes a distal flange (432) and a proximal flange (434), with a space defined between flanges (432, 434). In some other variations, each flange (432, 434) is in the form of an annular collar.

Guide element actuator (430) and dilation catheter actuator (420) are configured to cooperate with each other while providing some degree of lost motion. In particular, when dilation catheter actuator (420) is translated distally along a first range of motion as shown in the transition from FIG. 14A to FIG. 14B, dilation catheter (160) may advance distally while guide element (180) remains stationary (similar to what is shown in the transition from FIG. 2A to FIG. 2B and in the transition from FIG. 3A to FIG. 3B). During this transition, dilation catheter actuator (420) traverses the space between flanges (432, 434), eventually reaching distal flange (432). As dilation catheter actuator (420) is translated further distally along a second range of motion as shown in the transition from FIG. 14B to FIG. 14C, dilation catheter actuator (420) bears distally against distal flange (432), thereby driving guide element actuator (430) distally, which in turn drives guide element (180) distally with dilation catheter (160) (similar to what is shown in the transition from FIG. 2B to FIG. 2C and in the transition from FIG. 3B to FIG. 3C).

Figure 14A:
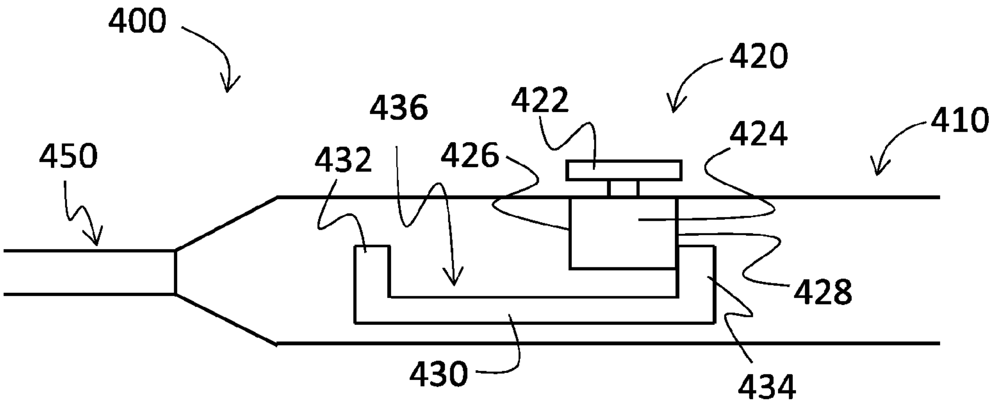
FIG. 14A depicts a schematic view of another example of a dilation instrument, with a dilation catheter actuator in a proximal position.
Figure 14B:
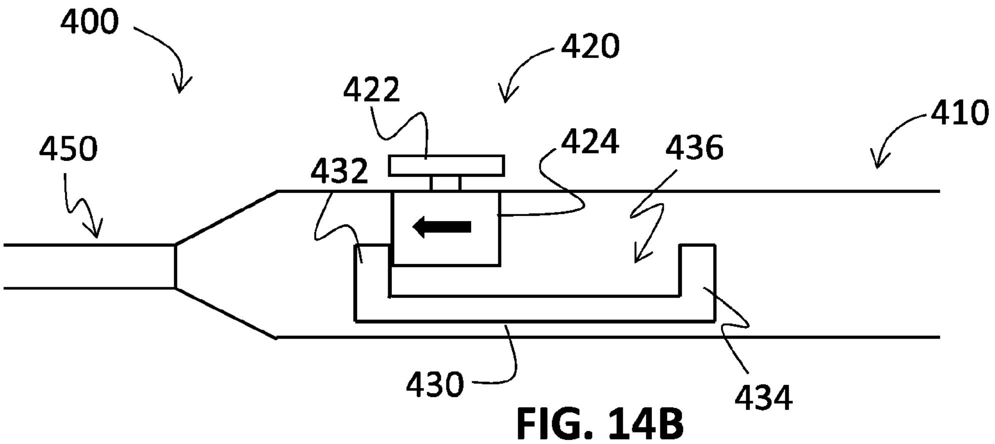
FIG. 14B depicts a schematic view of the dilation instrument of FIG. 14A, with the dilation catheter actuator at an intermediate longitudinal position en route from the proximal position of FIG. 14A to a distal position.
Figure 14C:
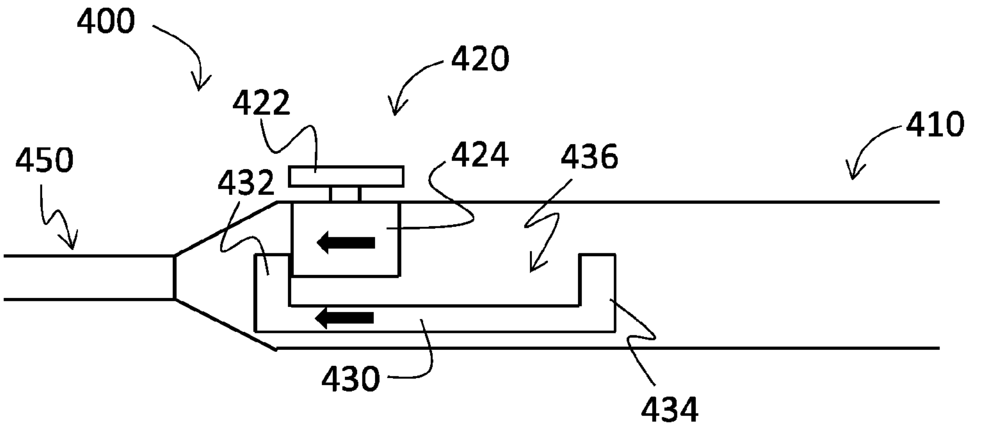
FIG. 14C depicts a schematic view of the dilation instrument of FIG. 14A, with the dilation catheter actuator at the distal position.
Figure 14D:
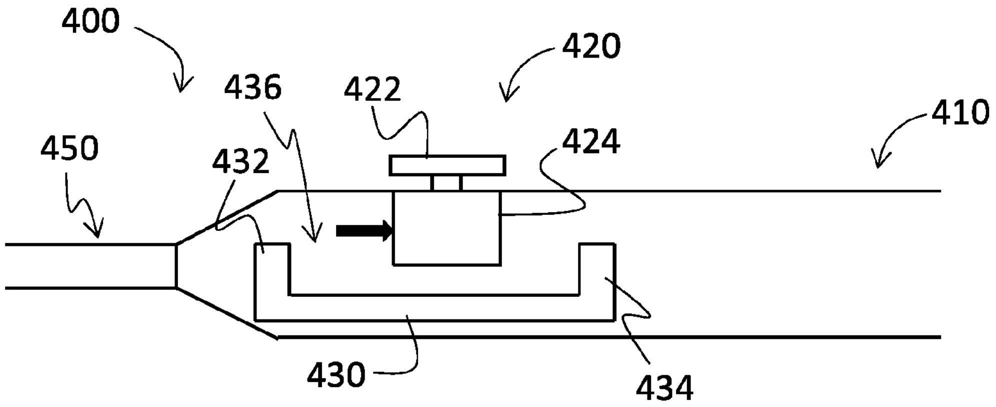
FIG. 14D depicts a schematic view of the dilation instrument of FIG. 14A, with the dilation catheter actuator at an intermediate longitudinal position en route from the distal position of FIG. 14C to the proximal position of FIG. 14A.
Figure 14E:
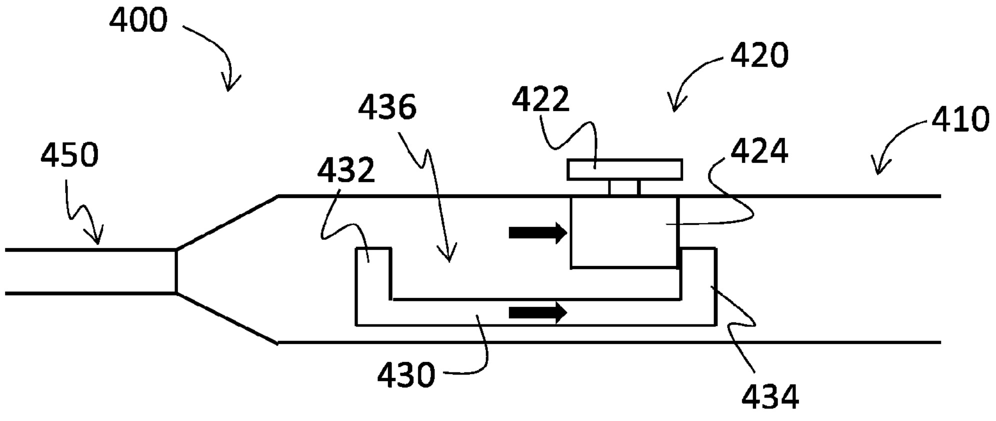
FIG. 14E depicts a schematic view of the dilation instrument of FIG. 14A, with the dilation catheter actuator returned to the proximal position of FIG. 14A from the intermediate longitudinal position of FIG. 14D.

When the operator retracts dilation catheter actuator (420) proximally along a first range of motion as shown the transition from FIG. 14C to FIG. 14D, dilation catheter actuator (420) traverses the space between flanges (432, 434). Thus, guide element actuator (430) and guide element (180) each remain in the distal position while dilation catheter actuator (420) and dilation catheter (160) retract proximally. As dilation catheter actuator (420) is translated further proximally, dilation catheter actuator (420) eventually engages proximal flange (434) and bears proximally against proximal flange (434), thereby driving guide element actuator (430) proximally as shown in the transition from FIG. 14D to FIG. 14E. This proximal movement of guide element actuator (430) returns guide element (180) to the proximal-most position shown in FIGS. 2E and 3E; while dilation catheter (160) also reaches the proximal-most position shown in FIGS. 2E and 3E.

Unlike the examples of instruments (100, 300) described above, instrument (400) of the present example does not provide a stage of operation during proximal retraction of dilation catheter (160) where guide element (180) and dilation catheter (160) translate together proximally from the distal-most position to an intermediate longitudinal position (similar to what is shown in the transition from FIG. 2C to FIG. 2D and the transition from FIG. 3C to FIG. 3D). However, the sequence of movements of dilation catheter (160) and guide element (180) is similar during the distal advancement of dilation catheter (160); and the relative positioning of dilation catheter (160) guide element (180) are also similar when dilation catheter (160) returns to the proximal-most position after reaching the distal-most position.

E. Example of Dilation Instrument with Dilation Catheter Actuator and Resiliently Biased Guide Element Actuator FIGS. 15A-15E show another example of an alternative dilation instrument (500).

Instrument (500) of this example may be configured and operable like instrument (100) described above, except for the differences described below. Instrument (500) of this example includes a body assembly (510) and a shaft assembly (550), which may be configured and operable similar to a body assembly (110) and a shaft assembly (150) of instrument (100). Body assembly (510) includes an internal boss (512) and a dilation catheter actuator (520). Dilation catheter actuator (520) may be coupled with dilation catheter (160) similar to the coupling between dilation catheter actuator (120) and dilation catheter (160) as described above. A guide element actuator (530) is slidably disposed in body assembly (310); and may be coupled with guide element (180) similar to the coupling between guide element actuator (190) and guide element (180) as described above.

Dilation catheter actuator (520) of the present example includes a finger pad (522) and a body (524). Finger pad (522) is positioned in an exterior region of body assembly (510) and is configured for engagement by the finger or thumb of the operator. Body (524) is positioned in an interior region of body assembly (510).

A biasing member (542) is fixedly secured within body assembly (510) and is coupled with guide element actuator (530) via an elongate member (540). Elongate member (540) and biasing member (542) cooperate to impart a proximal resilient bias on guide element actuator (530). By way of example only, elongate member (540) may comprise a pull-wire, a cable, a band, a strap, or any other suitable structure. Elongate member (540) is non-extensible in the present example, such that elongate member (540) will not stretch under tension. By way of further example only, biasing member (542) may comprise a spool or drum and a torsion spring and/or any other suitable components that are operable to maintain tension in elongate member (540) even as the effective length of elongate member (540) shortens during operation of instrument (500) as described in greater detail below. In some versions, due to a resilient proximal bias imparted on guide element actuator (530) by elongate member (540) and biasing member (542), guide element actuator (530) may bear proximally against internal boss (512) in the state shown in FIG. 15A. However, the fixed nature of internal boss (512) may prevent proximal movement of guide element actuator (530) from the position shown in FIG. 15A.

Figure 15A:
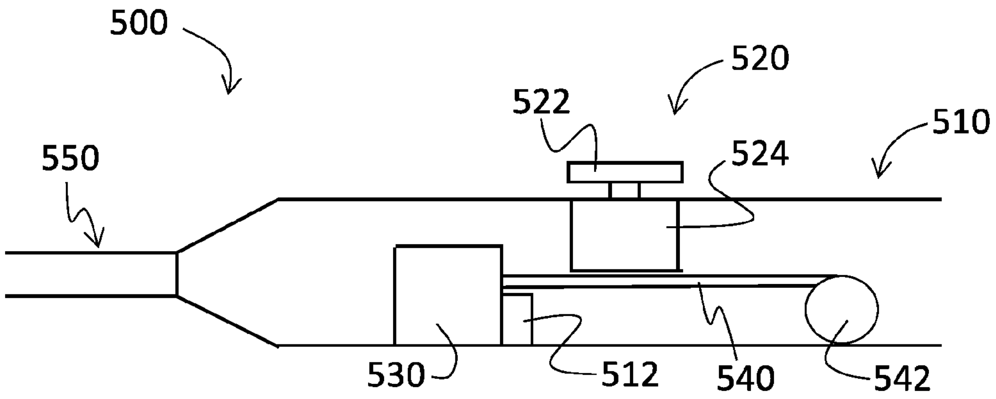
FIG. 15A depicts a schematic view of another example of a dilation instrument, with a dilation catheter actuator in a proximal position.
Figure 15B:
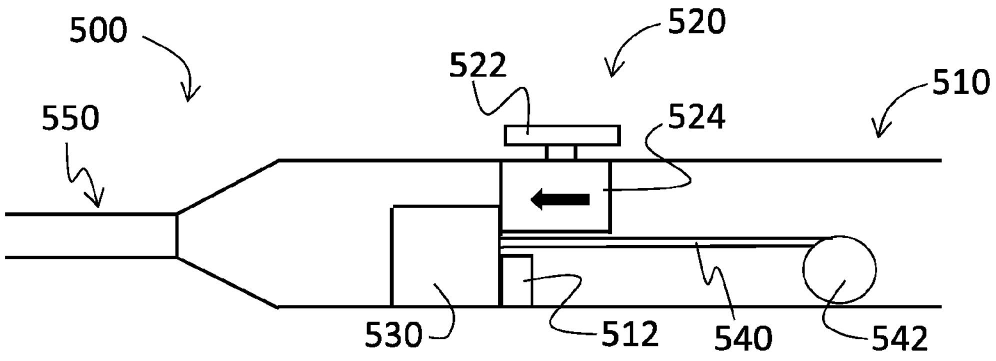
FIG. 15B depicts a schematic view of the dilation instrument of FIG. 15A, with the dilation catheter actuator at an intermediate longitudinal position en route from the proximal position of FIG. 15A to a distal position.

When dilation catheter actuator (520) is translated distally along a first range of motion as shown in the transition from FIG. 15A to FIG. 15B, dilation catheter (160) may advance distally while guide element (180) remains stationary (similar to what is shown in the transition from FIG. 2A to FIG. 2B and in the transition from FIG. 3A to FIG. 3B). Dilation catheter actuator (520) eventually engages guide element actuator (530) as shown in FIG. 15B. As dilation catheter actuator (520) is translated further distally along a second range of motion as shown in the transition from FIG. 15B to FIG. 15C, dilation catheter actuator (520) bears distally against guide element actuator (530), thereby driving guide element actuator (530) distally, which in turn drives guide element (180) distally with dilation catheter (160) (similar to what is shown in the transition from FIG. 2B to FIG. 2C and in the transition from FIG. 3B to FIG. 3C). Biasing member (542) maintains a proximal bias on guide element actuator (530) via elongate member (540) during the transition from the state shown in FIG. 15B to the state shown in FIG. 15C, yet biasing member (542) allows the effective length of elongate member (540) to increase (e.g., via unspooling, etc.), thereby allowing guide element actuator (530) to translate distally to the position shown in FIG. 15C.

Figure 15C:
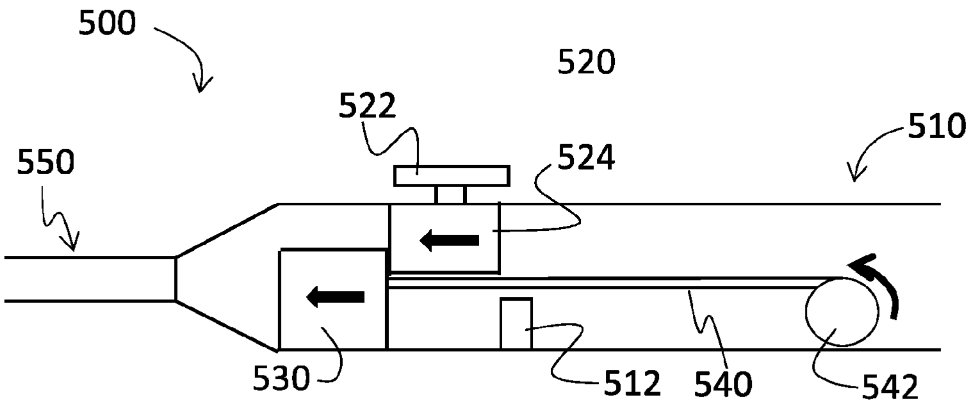
FIG. 15C depicts a schematic view of the dilation instrument of FIG. 15A, with the dilation catheter actuator at the distal position.
Figure 15D:
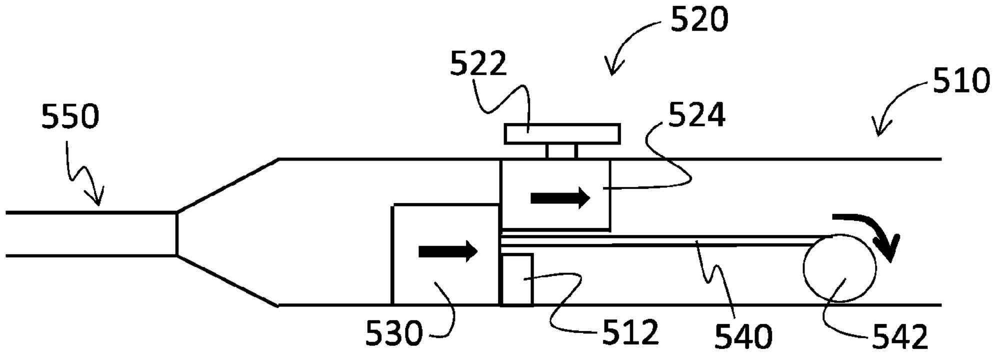
FIG. 15D depicts a schematic view of the dilation instrument of FIG. 15A, with the dilation catheter actuator at an intermediate longitudinal position en route from the distal position of FIG. 15C to the proximal position of FIG. 15A.
Figure 15E:
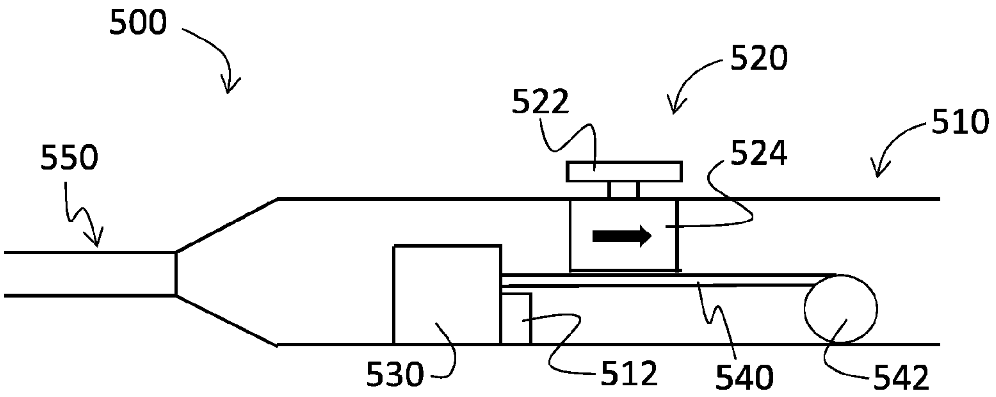
FIG. 15E depicts a schematic view of the dilation instrument of FIG. 15A, with the dilation catheter actuator returned to the proximal position of FIG. 15A from the intermediate longitudinal position of FIG. 15D.

When the operator retracts dilation catheter actuator (520) proximally along a first range of motion as shown the transition from FIG. 15C to FIG. 15D, the resilient proximal bias imparted by biasing member (542) and elongate member (540) on guide element actuator (530) guide element actuator (530) proximally, thereby driving guide element (180) proximally with dilation catheter (160) (similar to what is shown in the transition from FIG. 2C to FIG. 2D and in the transition from FIG. 3C to FIG. 3D). As dilation catheter actuator (520) is translated further proximally along a second range of motion as shown in the transition from FIG. 15D to FIG. 15E, guide element actuator (530) engages internal boss (512), such that internal boss (512) arrests further proximal movement of guide element actuator (530) and guide element (180). Dilation catheter actuator (520) and dilation catheter (160) continue translating proximally while guide element actuator (530) and guide element (180) remain stationary (similar to what is shown in the transition from FIG. 2D to FIG. 2E and in the transition from FIG. 3D to FIG. 3E).

III. Examples of Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a body assembly; (b) a first guide extending distally from the body assembly, the first guide having a distal end; (c) a dilation catheter slidably disposed relative to the first guide, the dilation catheter including: (i) an expandable element configured to dilate a passageway within a head of a patient, and (ii) a distal end; and (d) a second guide slidably disposed relative to the first guide and relative to the dilation catheter, the second guide including: (i) a distal end, and (ii) an indicator element, the indicator element being configured to indicate a position of the distal end of the second guide in three-dimensional space; the second guide being configured to position the indicator element at the distal end of the first guide and remain longitudinally stationary as the dilation catheter translates distally from a proximal position to an intermediate longitudinal position, the second guide being configured to translate concomitantly with the dilation catheter as the dilation catheter translates distally from the intermediate longitudinal position to a distal position, the indicator element being configured to be positioned with the distal end of the dilation catheter as the dilation catheter translates distally from the intermediate longitudinal position to a distal position.

Example 2

The apparatus of Example 1, the second guide being configured to translate concomitantly with the dilation catheter as the dilation catheter translates proximally from the distal position to the intermediate longitudinal position, the indicator element being configured to be positioned with the distal end of the dilation catheter as the dilation catheter translates distally from the distal position to the intermediate longitudinal position.

Example 3

The apparatus of Example 2, the second guide being configured to position the indicator element at the distal end of the first guide and remain longitudinally stationary as the dilation catheter translates proximally from the intermediate longitudinal position to the proximal position.

Example 4

The apparatus of Example 3, the body assembly comprising: (i) a housing, (ii) a dilation catheter actuator movable relative to the housing, the dilation catheter actuator being operable to drive longitudinal movement of the dilation catheter, and (iii) a second guide actuator movable relative to the housing, the second guide actuator being operable to drive longitudinal movement of the second guide.

Example 5

The apparatus of Example 4, the dilation catheter actuator comprising a first engagement feature, the second guide actuator comprising a second engagement feature, the first engagement feature being configured to engage the second engagement feature.

Example 6

The apparatus of Example 5, the first engagement feature being configured to engage the second engagement feature at the intermediate longitudinal position as the dilation catheter translates distally.

Example 7

The apparatus of Example 6, the first and second engagement features being configured to remain engaged as the dilation catheter translates distally from the intermediate longitudinal position to the distal position.

Example 8

The apparatus of Example 7, the first and second engagement features being configured to remain engaged as the dilation catheter translates proximally from the distal position to the intermediate longitudinal position.

Example 9

The apparatus of Example 8, the first engagement feature being configured to disengage from the second engagement feature when the dilation catheter translates proximally from the intermediate longitudinal position to the proximal position.

Example 10

The apparatus of Example 9, the body assembly further comprising a boss, the second guide actuator being configured to engage the boss at the intermediate longitudinal position as the dilation catheter translates proximally, the boss being configured to arrest further proximal movement of the second guide actuator.

Example 11

The apparatus of any of Examples 5 through 10, the first engagement the first and second engagement features being configured to removably coupled together via a friction fit.

Example 12

The apparatus of Example 11, one of the first and second engagement features comprising a peg, the other of the first and second engagement features comprising a recess, the recess being configured to receive the peg through a friction fit.

Example 13

The apparatus of Example 12, the peg being integrated into the second guide actuator, the recess being formed in the dilation catheter actuator.

Example 14

The apparatus of any of Examples 5 through 10, the first engagement feature including a resiliently biased member.

Example 15

The apparatus of Example 14, the resiliently biased member comprising a ball.

Example 16

The apparatus of any of Examples 14 through 15, the second engagement feature comprising a recess configured to receive the resiliently biased member.

Example 17

The apparatus of any of Examples 5 through 10, the first and second engagement features being configured to magnetically coupled together.

Example 18

The apparatus of Example 17, the first engagement feature comprising a first magnet, the second engagement feature comprising a second magnet.

Example 19

The apparatus of any of Examples 4 through 10, the body assembly further comprising an elongate member and a biasing member, the elongate member and the biasing member being configured to impart a resilient proximal bias on the second guide actuator.

Example 20

The apparatus of Example 19, the elongate member comprising an element selected from the group consisting of a pull-wire, a cable, a band, and a strap.

Example 21

The apparatus of any of Examples 19 through 20, the biasing member comprising a torsion spring.

Example 22

The apparatus of Example 21, the biasing member further comprising a spool or a drum, the elongate member being configured to wind about the spool or drum.

Example 23

The apparatus of any of Examples 1 through 22, the first guide comprising a guide rail, the dilation catheter being slidably disposed about an exterior of the guide rail.

Example 24

The apparatus of any of Examples 1 through 23, a distal portion the first guide being malleable to enable the distal portion of the first guide to define a selected bend angle.

Example 25

The apparatus of any of Examples 1 through 24, the indicator element comprising a position sensor, the position sensor being configured to generate a signal indicating a position of the position sensor in three-dimensional space.

Example 26

The apparatus of Example 25, the position sensor comprising one or more coils.

Example 27

The apparatus of any of Examples 1 through 26, the indicator element comprising an illuminating feature configured to provide transillumination through tissue of a patient.

Example 28

The apparatus of Example 27, the second guide further comprising an optical fiber in optical communication with the indicator element.

Example 29

The apparatus of Example 27, the illuminating feature comprising an LED at the distal end of the second guide.

Example 30

The apparatus of any of Examples 1 through 29, the indicator element being positioned at the distal end of the second guide.

Example 31

The apparatus of Example 1, the second guide being configured to remain longitudinally stationary as the dilation catheter translates proximally form the distal position to a second intermediate longitudinal position.

Example 32

The apparatus of Example 31, the second guide being configured to translate concomitantly with the dilation catheter as the dilation catheter translates proximally from the second intermediate longitudinal position to the proximal position.

Example 33

The apparatus of any of Examples 31 through 32, the body assembly comprising: (i) a housing, (ii) a dilation catheter actuator movable relative to the housing, the dilation catheter actuator being operable to drive longitudinal movement of the dilation catheter, and (iii) a second guide actuator movable relative to the housing, the second guide actuator being operable to drive longitudinal movement of the second guide, the second guide actuator comprising a distal engagement feature and a proximal engagement feature, the dilation catheter actuator being configured to translate through a space defined between the distal engagement feature and the proximal engagement feature.

Example 34

The apparatus of Example 33, the dilation catheter actuator being configured to bear against the distal engagement feature and thereby drive the second guide actuator distally as the dilation catheter translates distally from the intermediate longitudinal position to the distal position.

Example 35

The apparatus of any of Examples 33 through 34, the second guide being configured to translate concomitantly with the dilation catheter as the dilation catheter translates proximally from the second intermediate longitudinal position to the proximal position, the dilation catheter actuator being configured to bear against the proximal engagement feature and thereby drive the second guide actuator proximally as the dilation catheter translates proximally from the second intermediate longitudinal to the proximal position.

Example 36

An apparatus, comprising: (a) a body assembly; (b) a first guide extending distally from the body assembly, the first guide having a distal end; (c) a dilation catheter slidably disposed relative to the first guide, the dilation catheter including: (i) an expandable element configured to dilate a passageway within a head of a patient, and (ii) a distal end; and (d) a second guide slidably disposed relative to the first guide and relative to the dilation catheter, the second guide including: (i) a distal end, and (ii) an indicator element, the indicator element being configured to indicate a position of the distal end of the second guide in three-dimensional space; the second guide being configured to position the distal end of the second guide at the distal end of the first guide and remain longitudinally stationary as the dilation catheter translates distally from a proximal position to an intermediate longitudinal position, the second guide being configured to translate concomitantly with the dilation catheter as the dilation catheter translates distally from the intermediate longitudinal position to a distal position, the distal end of the second guide being configured to be positioned with the distal end of the dilation catheter as the dilation catheter translates distally from the intermediate longitudinal position to a distal position.

Example 37

The apparatus of Example 36, the second guide being configured to translate concomitantly with the dilation catheter as the dilation catheter translates proximally from the distal position to the intermediate longitudinal position, the distal end of the second guide being configured to be positioned with the distal end of the dilation catheter as the dilation catheter translates distally from the distal position to the intermediate longitudinal position.

Example 38

The apparatus of Example 37, the second guide being configured to position the distal end of the second guide at the distal end of the first guide and remain longitudinally stationary as the dilation catheter translates proximally from the intermediate longitudinal position to the proximal position.

Example 39

A method comprising: (a) inserting a shaft assembly of an instrument into a head of a patient, thereby positioning a first guide of the instrument in an anatomical passageway in the head of the patient, an indicator element of a second guide indicating a position of the distal end of the first guide in three-dimensional space during at least part of the act of inserting; (b) advancing a dilation catheter distally relative to the first guide through a first range of distal motion from a proximal position to an intermediate longitudinal position, a distal end of the dilation catheter being proximal to the distal end of the first guide as the dilation catheter advances distally from the proximal position, the distal end of the dilation catheter being at the same longitudinal position as the distal end of the first guide after the dilation catheter reaches the intermediate longitudinal position; (c) advancing the dilation catheter distally relative to the first guide through a second range of distal motion from the intermediate longitudinal position to a distal position, the distal end of the dilation catheter being distal to the distal end of the first guide as the dilation catheter advances distally from the intermediate longitudinal position to the distal position, the second guide translating concomitantly with the dilation catheter as the dilation catheter translates distally from the intermediate longitudinal position to the distal position, the indicator element indicating a position of the distal end of the dilation catheter in three-dimensional space during at least part of the act of advancing the dilation catheter distally relative to the first guide through the second range of distal motion; and (d) expanding a dilator of the dilation catheter while the dilation catheter is at the distal position.

Example 40

The method of Example 49, further comprising retracting the dilation catheter proximally through a first range of proximal motion from the distal position to the intermediate longitudinal position, the second guide translating concomitantly with the dilation catheter as the dilation catheter retracts proximally from the distal position to the intermediate longitudinal position, the indicator element indicating a position of the distal end of the dilation catheter in three-dimensional space during at least part of the act of retracting the dilation catheter proximally through the first range of proximal motion.

Example 41

The method of Example 40, further comprising retracting the dilation catheter proximally through a second range of proximal motion from the intermediate longitudinal position to the proximal position, the second guide remaining longitudinally stationary as the dilation catheter translates proximally from the intermediate longitudinal position to the proximal position, the indicator element indicating a position of the distal end of the first guide in three-dimensional space during at least part of the act of retracting the dilation catheter proximally through the second range of proximal motion.

Example 42

The method of any of Examples 39 through 41, the indicator element generating signals indicating position data via an image guided surgery system.

Example 43

The method of any of Examples 39 through 42, the indicator element providing transillumination through tissue of the patient.

Example 44

The method of any of Examples 39 through 43, the anatomical passageway comprising a Eustachian tube or a passageway associated with drainage of a paranasal sinus.

Example 45

The method of any of Examples 39 through 43, further comprising bending the first guide to achieve a bend angle before inserting the shaft assembly in the head of the patient, the first guide being malleable and thereby maintaining the bend angle during the acts of inserting. advancing the dilation catheter distally relative to the first guide through the first range of distal motion, advancing the dilation catheter distally relative to the first guide through the second range of distal motion, and expanding the dilator.

IV. Miscellaneous

It should be understood that any of the teachings, expressions, embodiments, examples, etc. described herein may be combined with any of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:

a body assembly;

a first guide extending distally from the body assembly, the first guide having a distal end;

a dilation catheter slidably disposed relative to the first guide, the dilation catheter including:

(i) an expandable element configured to dilate a passageway within a head of a patient, and (ii) a distal end; and a second guide slidably disposed relative to the first guide and relative to the dilation catheter, the second guide including:

(i) a distal end, and (ii) an indicator element, the indicator element being configured to indicate a position of the distal end of the second guide in three-dimensional space;

the body assembly further including:

a housing, a dilation catheter actuator being movable relative to the housing and operable to drive longitudinal movement of the dilation catheter, and a second guide actuator being movable relative to the housing and operable to drive longitudinal movement of the second guide, the second guide actuator comprising a distal engagement feature and a proximal engagement feature defining a space therebetween, the dilation catheter actuator being configured to translate through the space without coupling to the second guide actuator, the second guide being configured to position the indicator element at the distal end of the first guide and remain longitudinally stationary as the dilation catheter translates distally from a proximal position to an intermediate longitudinal position, the second guide being configured to translate concomitantly with the dilation catheter as the dilation catheter translates distally from the intermediate longitudinal position to a distal position, the indicator element being configured to be positioned with the distal end of the dilation catheter as the dilation catheter translates distally from the intermediate longitudinal position to a distal position.

2. The apparatus of claim 1, the second guide being configured to translate concomitantly with the dilation catheter as the dilation catheter translates proximally from the distal position to the intermediate longitudinal position, the indicator element being configured to be positioned with the distal end of the dilation catheter as the dilation catheter translates distally from the distal position to the intermediate longitudinal position.

3. The apparatus of claim 2, the second guide being configured to position the indicator element at the distal end of the first guide and remain longitudinally stationary as the dilation catheter translates proximally from the intermediate longitudinal position to the proximal position.

4. The apparatus of claim 1, the dilation catheter actuator comprising a first engagement feature, the second guide actuator comprising a second engagement feature, the first engagement feature being configured to engage the second engagement feature.

5. The apparatus of claim 4, the first engagement feature being configured to engage the second engagement feature at the intermediate longitudinal position as the dilation catheter translates distally.

6. The apparatus of claim 5, the first and second engagement features being configured to remain engaged as the dilation catheter translates distally from the intermediate longitudinal position to the distal position.

7. The apparatus of claim 4, the first and second engagement features being configured to be removably coupled together via a friction fit.

8. The apparatus of claim 4, the first engagement feature including a resiliently biased member.

9. The apparatus of claim 4, the first and second engagement features being configured to be magnetically coupled together.

10. The apparatus of claim 1, the first guide comprising a guide rail, the dilation catheter being slidably disposed about an exterior of the guide rail.

11. The apparatus of claim 1, a distal portion of the first guide being malleable to enable the distal portion of the first guide to define a selected bend angle.

12. The apparatus of claim 1, the indicator element comprising a position sensor, the position sensor being configured to generate a signal indicating a position of the position sensor in three-dimensional space.

13. The apparatus of claim 1, the indicator element comprising an illuminating feature configured to provide transillumination through tissue of a patient.

14. The apparatus of claim 1, wherein the second guide is configured to (i) remain longitudinally stationary as the dilation catheter translates proximally from the distal position to the intermediate position, and (ii) translate concomitantly with the dilation catheter as the dilation catheter translates proximally from the intermediate position to the proximal position.

15. An apparatus, comprising:

a body assembly;

a first guide extending distally from the body assembly, the first guide having a distal end;

a dilation catheter slidably disposed relative to the first guide, the dilation catheter including:

(i) an expandable element configured to dilate a passageway within a head of a patient, and (ii) a distal end; and a second guide slidably disposed relative to the first guide and relative to the dilation catheter, the second guide including:

(i) a distal end, and (ii) an indicator element, the indicator element being configured to indicate a position of the distal end of the second guide in three-dimensional space;

the body assembly further including:

a housing, a dilation catheter actuator being movable relative to the housing and operable to drive longitudinal movement of the dilation catheter, and a second guide actuator being movable relative to the housing and operable to drive longitudinal movement of the second guide, the second guide actuator comprising a distal engagement feature and a proximal engagement feature defining a space therebetween, the dilation catheter actuator being configured to translate through the space without coupling to the second guide actuator, the second guide being configured to position the distal end of the second guide at the distal end of the first guide and remain longitudinally stationary as the dilation catheter translates distally from a proximal position to an intermediate longitudinal position, the second guide being configured to translate concomitantly with the dilation catheter as the dilation catheter translates distally from the intermediate longitudinal position to a distal position, the distal end of the second guide being configured to be positioned with the distal end of the dilation catheter as the dilation catheter translates distally from the intermediate longitudinal position to a distal position.

* * * * *